US 7,745,417 B2

(12) United States Patent
Hirao et al.

(10) Patent No.: US 7,745,417 B2
(45) Date of Patent: Jun. 29, 2010

(54) NUCLEOSIDES OR NUCLEOTIDES HAVING NOVEL UNNATURAL BASES AND USE THEREOF

(75) Inventors: Ichiro Hirao, Wako (JP); Shigeyuki Yokoyama, Yokohama (JP); Michiko Hirao, Wako (JP); Tsuneo Mitsui, Wako (JP)

(73) Assignees: RIKEN, Wako-shi (JP); Japan Science and Technology Agency, Kawaguchi-shi (JP)

( * ) Notice: Subject to any disclaimer, the term of this patent is extended or adjusted under 35 U.S.C. 154(b) by 331 days.

(21) Appl. No.: 10/521,454

(22) PCT Filed: Feb. 28, 2003

(86) PCT No.: PCT/JP03/02342

§ 371 (c)(1),
(2), (4) Date: Nov. 29, 2005

(87) PCT Pub. No.: WO2004/007713

PCT Pub. Date: Jan. 22, 2004

(65) Prior Publication Data

US 2006/0263771 A1 Nov. 23, 2006

(30) Foreign Application Priority Data

Jul. 17, 2002 (JP) .............................. 2002-208568

(51) Int. Cl.
*A61K 31/70* (2006.01)
*C07H 19/00* (2006.01)
*C07H 21/00* (2006.01)
*C07H 21/02* (2006.01)

(52) U.S. Cl. ........................ 514/44; 536/22.1; 536/23.1; 536/25.3

(58) Field of Classification Search ........................ None
See application file for complete search history.

(56) References Cited

U.S. PATENT DOCUMENTS 6,447,998 B1 * 9/2002 Froehler et al. ................. 435/6
6,495,672 B1 * 12/2002 Froehler et al. ............ 536/23.1
2003/0120065 A1 * 6/2003 Froehler et al. ............ 536/29.2

FOREIGN PATENT DOCUMENTS

WO    WO-01/16149 A    3/2001

OTHER PUBLICATIONS

Ohtsuki et al. PNAS, Apr. 2001, vol. 98, No. 9, pp. 4922-4925.*
Guo et al. Nucleic Acids Research 1998, vol. 26, No. 8, pp. 1863-1869.*
Battersby et al., J. Am. Chem. Soc., vol. 121, (1999), pp. 9781-9789.
Campbell et al., Oncogene, vol. 17, (1998), pp. 1395-1413.
Chen et al., Anal. Chem., vol. 28, (1956), pp. 1756-1758.
Ellington et al., Nature, vol. 346, (1990), pp. 818-822.
Fang et al., Anal. Chem., vol. 73, (2001), pp. 5752-5757.
Fujiwara et al., Bioorg. Med. Chem. Lett. vol. 11, (2001), pp. 2221-2223.
Golden et al., Journal of Biotechnology, vol. 81, (2000), pp. 167-178.
Hirao et al., J. Biol. Chem., vol. 275, (2000), pp. 4943-4948.
Hirao et al., Chem. Lett., (2001), pp. 914-915.
Hirao et al., Nature Biotechnol., vol. 20, (2002), pp. 177-182.
Inouye et al., J. Biol. Chem., vol. 275, (2000), pp. 3737-3740.
Ishikawa et al., Tetrahedron Letters, vol. 41, (2000), pp. 3931-3034.
Jensen et al., Proc. Natl. Acad. Sci. USA, vol. 92, (1995), pp. 12220-12224.
Jhaveri et al., Nature Biotechnology, vol. 18, (2000), pp. 1293-1297.
Kolch, Biochem. J., vol. 351, (2000), pp. 289-305.
Koyama et al., FEBS Letters, vol. 380, (1996), pp. 113-117.
Latham et al., Nucleic Acids Research, vol. 22, (1994), pp. 2817-2822.
Ludwig et al., J. Org. Chem., vol. 54, (1989), pp. 631-635.
Matulic-Adamic et al., Tetrahedron Letters, vol. 38, (1997), pp. 203-206.
Meisenheimer et al., Crit. Rev. Biochem. Mol. Biol., vol. 32, (1997), pp. 101-140.
Morales et al., J. Am. Chem. Soc., vol. 121, (1999), pp. 2323-2324.
Ohtsuki et al., Proc. Natl. Acad. Sci. USA, vol. 98, (2001), pp. 4922-4925.
Piccirilli et al., Nature, vol. 343, (1990), pp. 33-37.
Piccirilli et al., Biochemistry, vol. 30, (1991), pp. 10350-10356.
Rapp et al., Cold Spring Harb. Symp. Quant. Biol., vol. 53, (1988), pp. 173-184.
Switzer et al., Biochemistry, vol. 32, (1993), pp. 10489-10496.
Tae et al., J. Am. Chem. Soc., vol. 123, (2001), pp. 7439-7440.
Wu et al., J. Am. Chem. Soc., vol. 122, (2000), pp. 7621-7632.
Yamamoto et al., Genes to Cells, vol. 5, (2000), pp. 389-396.
Broekman et al., Recueil, vol. 81, (1962), pp. 107-111.
Gott et al., Biochemistry, vol. 30, (1991), pp. 6290-6295.
Petach et al., Current Opinion in Biotechnology, vol. 13, (2002), pp. 309-314.
Brody et al., Molecular Diagnosis, vol. 4, (1999), pp. 381-388.
Theissen et al., Anal. Biochem., vol. 179, (1989), pp. 98-105.
Bellinzoni et al., Mol. Cell. Probes, Vol. 3, (1989), pp. 233-244.
Langer et al., Proc. Natl. Acad. Sci. USA, vol. 78, (1981), pp. 6633-6637.
Ruby et al., Methods in Enzymology, vol. 181, (1990), pp. 97-121.

(Continued)

*Primary Examiner*—Janet L. Epps-Smith
(74) *Attorney, Agent, or Firm*—Birch, Stewart, Kolasch & Birch, LLP

(57) ABSTRACT

The object of the present invention is to provide a nucleoside or nucleotide having an unnatural base. The nucleoside or nucleotide of the present invention has a 5-substituted-2-oxo (1H)-pyridin-3-yl group as a base. Preferably, the 5-position of the above base is substituted with a substituent selected from the group consisting of the following:

1) a photoreactive group selected from iodine and bromine;
2) an alkenyl group, an alkynyl group or an amino group, or a derivative thereof;
3) biotin or a derivative thereof; and
4) a fluorescent molecule selected from fluorescein, 6-carboxyfluorescein, tetramethyl-6-carboxyrhodamine, and derivatives thereof.

30 Claims, 20 Drawing Sheets

OTHER PUBLICATIONS

Huang et al., RNA, vol. 9, (2003), pp. 1562-1570.
Ichiro Hirao at al., Protein, Nucleic acid and Enzyme, vol. 47, No. 14, pp. 1904 to 1913 (Nov. 2002).
I. Hirao et al., Bioorganic & Medicinal Chemistry Letters, vol. 12, pp. 1391 to 1393, (May 2002).
Silverman et al., "Molecular Moment Similarity Between Several Nucleoside Analogs of Thymidine and Thymidine", Journal of Biomolecular Structure & Dynamics, ISSN 0739-1102, vol. 16, No. 6, pp. 1169-1175, 1999, Yorktown Heights, NY.

* cited by examiner

Figure 1
a) 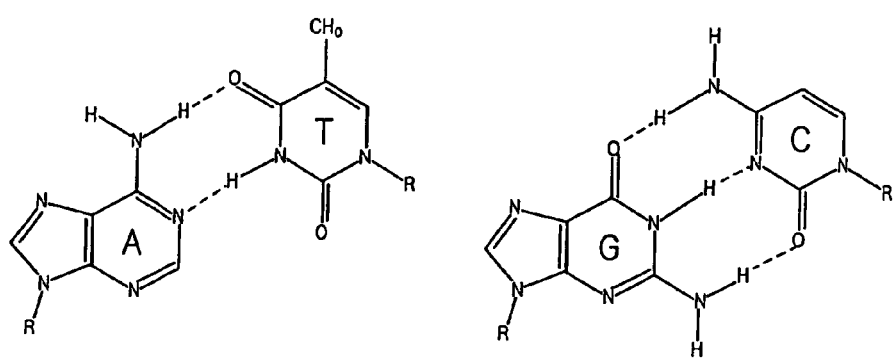
b) 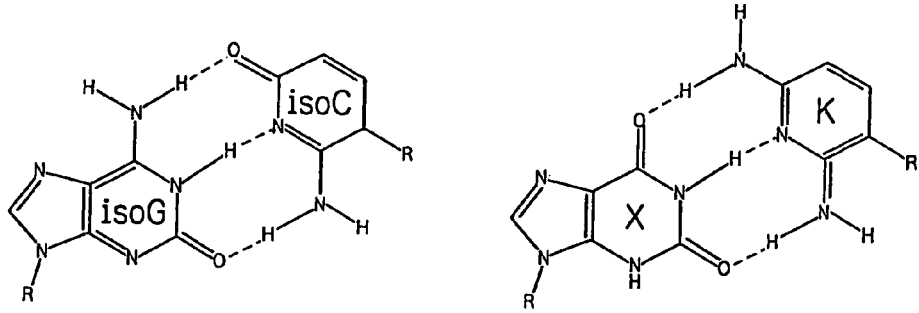
c) 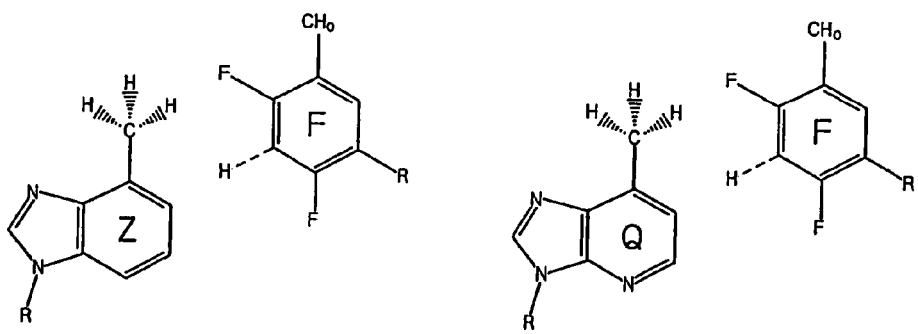
d) 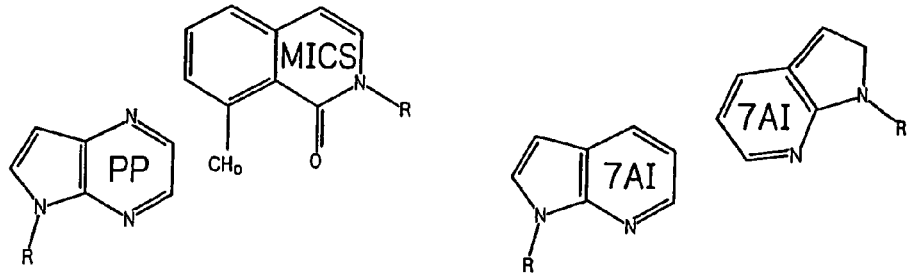

(a) $I_2$, KI, $Na_2CO_3$, 100°C, 4h. (b) $CF_3CONHCH_2CCH$, $Pd(Ph_3P)_4$, CuI, $Et_3N$, DMF, rt, 4-6h. (c)(1) $POCl_3$, $(CH_3O)_3PO$, 0°C, 2h. (2) $(n-Bu_3NH)_2P_2O_7$, 0°C, 10min. (d)(1) $POCl_3$, 1,8-bis(dimethylamino)naphthalene, $(CH_3O)_3PO$, 0°C, 2h. (2) $(n-Bu_3NH)_2P_2O_7$, 0°C, 10min. (3) conc. $NH_4OH$, rt, 10h.

Figure 4
a)
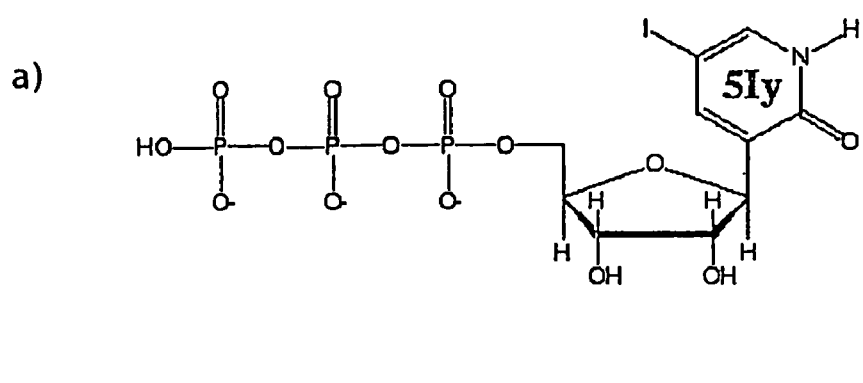
b)
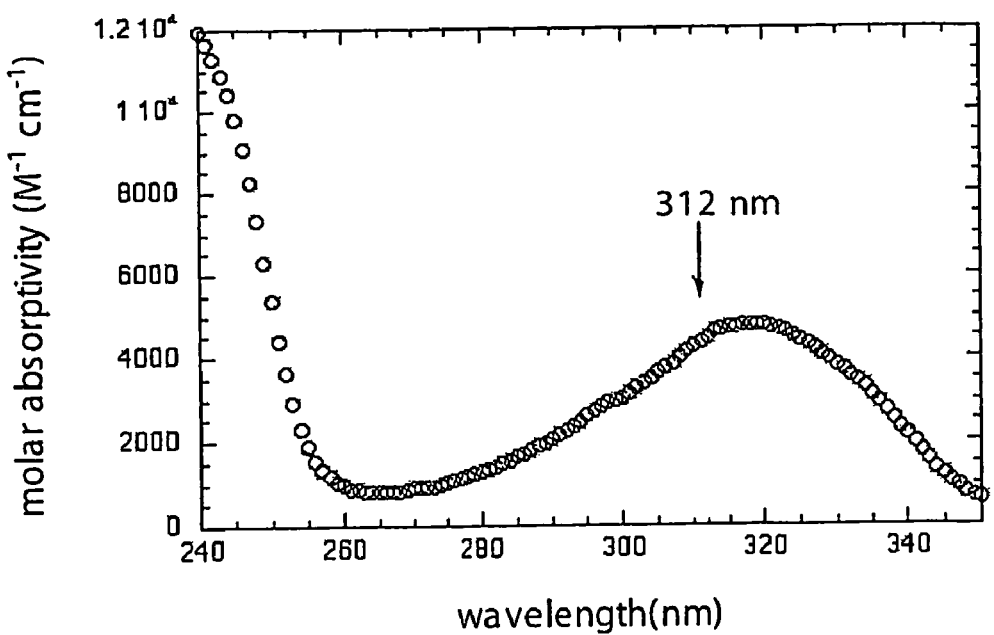

Figure 5 a)

5'-end primer; 39-mer 39.45 : 5'-GGTAATACGACTCACTATAGGGAGTGGAGGAATTCATCG

3'-end primer; 29-mer 29.45      :5'-GCAGAAGCTTGCTGTCGCTAAGGCATATG
29.45s84   :5'-GCAGAAGCTTGCTGTCsCTAAGGCATATG
29.45s87   :5'-GCAGAAGCTTGCTsTCGCTAAGGCATATG
29.45s92   :5'-GCAGAAGCsTGCTGTCGCTAAGGCATATG
29.45s84/92:5'-GCAGAAGCsTGCTGTCsCTAAGGCATATG b)

5'- GGGAGUGGAG GAAUUCAUCG AGGCAUAUGU CGACUCCGUC UUCCUUCAAA
    CCAGUUAUAA AUUGGUUUUA GCAUAUGCCU UAGCGACAGC AAGCUUCUGC

Figure 6
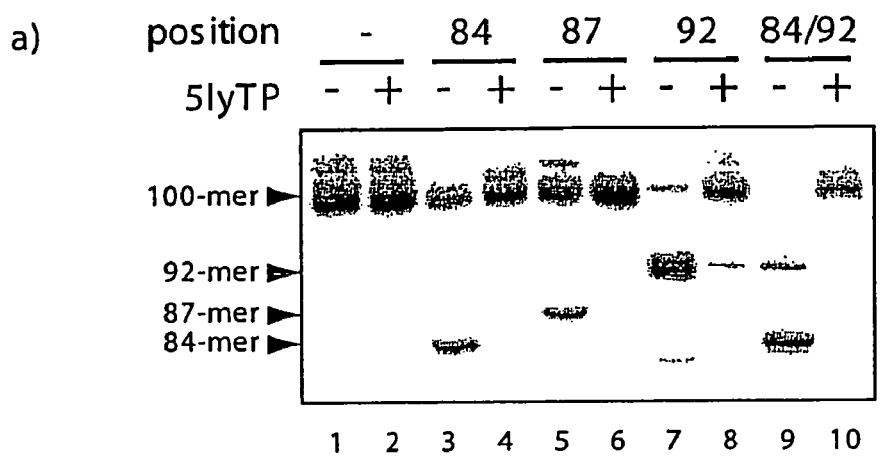
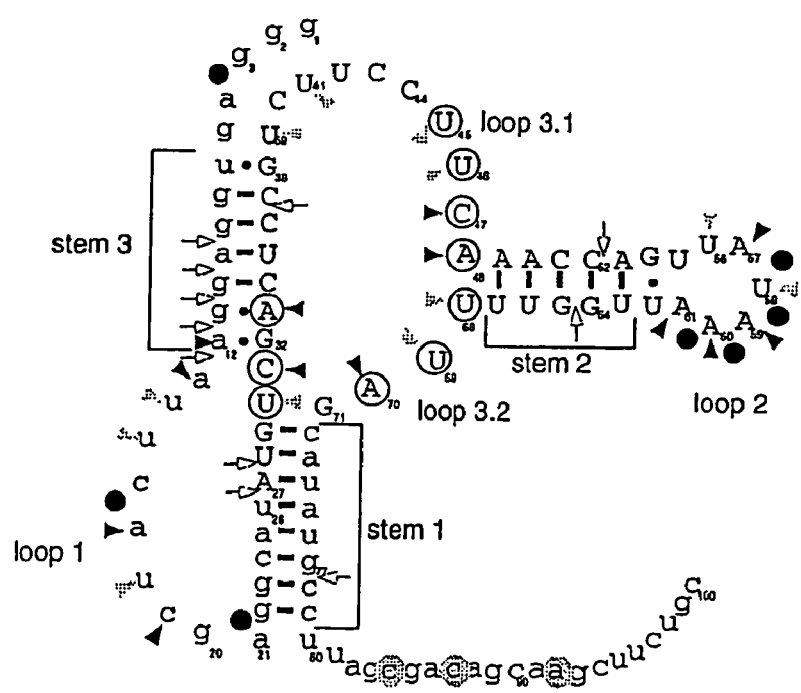

Figure 10

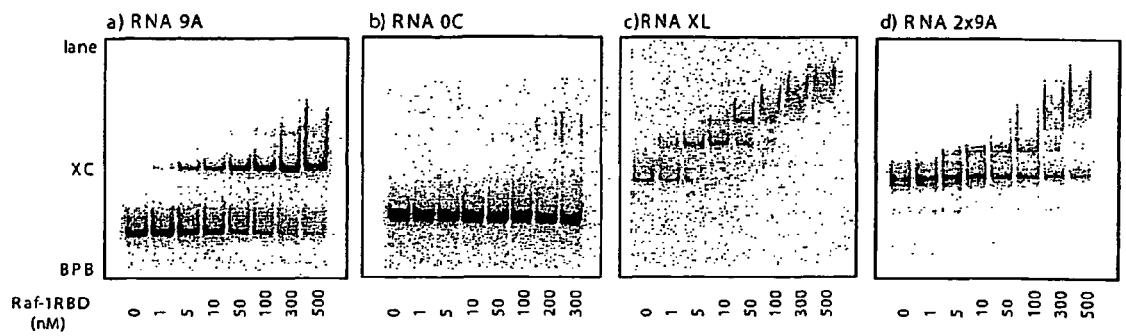

e) RNA 9A :100-mer
5'-GGGAGUGGAGGAAUUCAUCGAGGCAU[-N4s-]CAUAUGCCUUAGCGACAGCAAGCUUCUGC-3'
AUGUCGACUCCGUCUUCCUUCAAACCAGUUAUAAAUUGGUUUUAG RNA 9A(5Iy87) :100-mer
5'-GGGAGUGGAGGAAUUCAUCGAGGCAU[-N4s-]cauaugccuuagcga5IyCAGCAAGCUUCUGC-3'

RNA 2x9A :200-mer
5'-GGGAGUGGAGGAAUUCAUCGAGGCAU[-N4s-]CAUAUGCCUUAGCGACAGCAAGCUUCUGC-
-GGGAGUGGAGGAAUUCAUCGAGGCAU[-N4s-]CAUAUGCCUUAGCGACAGCAAGCUUCUGC-3'

RNA 0C :100-mer
5'-GGGAGUGGAGGAAUUCAUCGAGGCAU[-N4s-]CAUAUGCCUUAGCGACAGCAAGCUUCUGC-3'
CUGGGAACCCUAUCUUGCUUUUGGUAGCUGUAUUCACCUGUAACAG RNA XL : cross-linking product generated from two molecules of 9A(5Iy87)

Figure 14
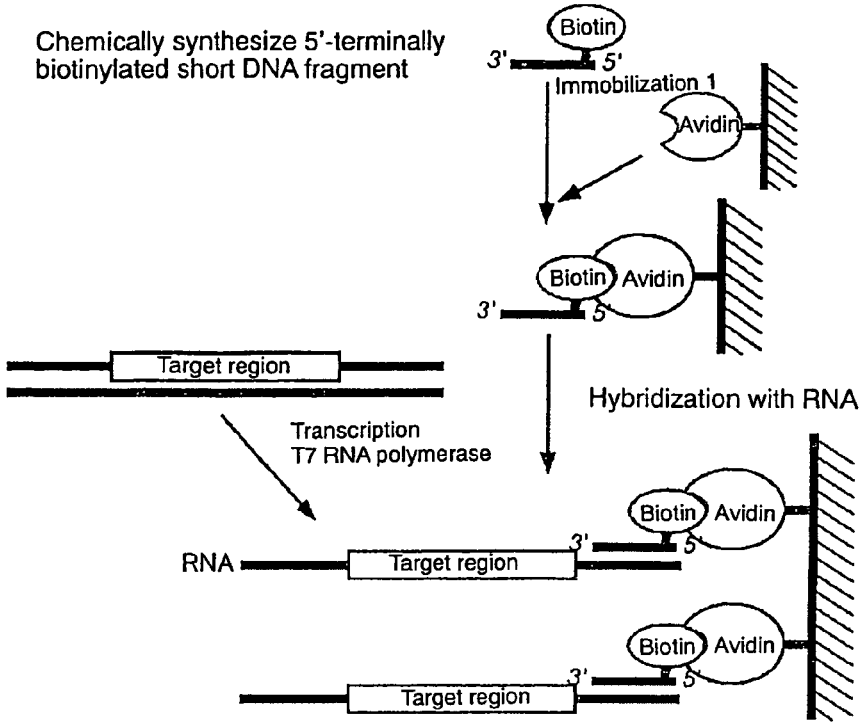
Conventional Method 1
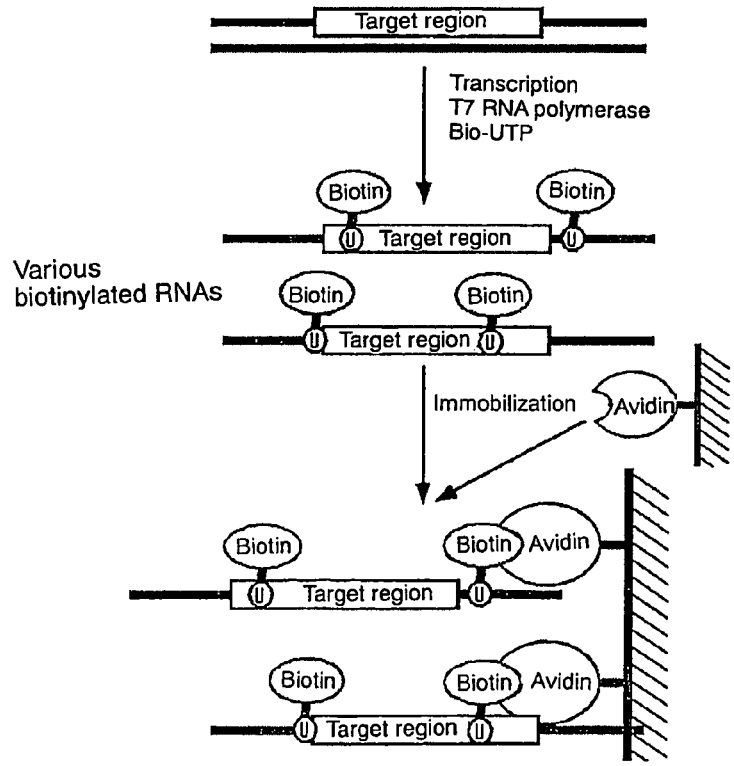
Conventional Method 2

NUCLEOSIDES OR NUCLEOTIDES HAVING NOVEL UNNATURAL BASES AND USE THEREOF

TECHNICAL FIELD

The present invention relates to nucleosides or nucleotides having novel unnatural bases and use thereof.

BACKGROUND ART

In nucleic acids (DNA, RNA) which are biological macromolecules, enormous amounts of genetic information essential for vital activities are recorded as sequences composed of combinations of only 4 bases. Such a nucleic acid allows self-replication using itself as a template by the action of DNA polymerase, and further undergoes processes of RNA polymerase-mediated transcription and ribosome-mediated translation to ensure the transmission of genetic information from DNA to DNA, from DNA to RNA, and/or from RNA to protein. It is exclusive base-pairing rules (A:T/U, G:C) that enable these replication and transmission events of genetic information. In addition, nucleic acids can form a variety of higher-order structures and hence exert various functions. By way of example, it is one of the indications that a large number of novel nucleic acids having aptamer and/or ribozyme functions have been generated by in vitro selection techniques.

However, unlike proteins which are composed of 20 types of amino acids, the chemical and physical diversity of nucleic acids is limited by the fact that there are only 4 bases (2 base pairs) in natural nucleic acids. For example, functional RNAs (e.g., tRNA, rRNA, mRNA) found in living bodies utilize various modified bases to stabilize their own structure and/or RNA-RNA and RNA-protein interactions. Thus, it will be very advantageous to expand the repertory of new bases (base pairs) in developing novel functional nucleic acids.

With the aim of further expansion of nucleic acid functions, attempts have been made to design nucleosides or nucleotides having unnatural bases. There are two possible approaches for introducing modified bases (or unnatural bases) into nucleic acids: 1) direct introduction by chemical synthesis; and 2) introduction catalyzed by nucleic acid polymerase enzymes. In the case of 1), there is a need to solve some problems associated with chemical synthesis, such as the stability of amidite units and the presence of protecting groups appropriate for base moieties. If these problems are solved, various unnatural bases can be introduced in a site-selective manner. However, the nucleic acids thus obtained are difficult to amplify and it is also difficult to synthesize long-chain nucleic acids. In the case of 2), if the enzymes recognize substrates to cause replication and transcription between artificial base pairs in a complementary manner, nucleic acids containing such artificial base pairs can be amplified and prepared. However, such substrates and base pairs (unnatural nucleitides) are still under development.

BACKGROUND OF UNNATURAL ARTIFICIAL BASE PAIRS

The combinations A:T and G:C found in natural double-stranded DNA each form an "exclusive" base pair through specific hydrogen bonding (FIG. 1a). The group of Benner et al. focused on the pattern of hydrogen bonding and designed novel base pairs based on different hydrogen-bonding combinations from those of natural base pairs. For example, isoG:isoC and κ:X base pairs (FIG. 1b) have been reported and analyzed for their incorporation into DNA and/or RNA molecules by the action of various nucleic acid polymerase enzymes. [Piccirilli et al., 1990; Piccirilli et al., 1991; Switzer et al., 1993].

However, these unnatural base pairs suffer from the following or other problems: 1) isoG causes keto-enol tautomerism between 1- and 2-positions and hence forms a base pair with T; 2) as indicated by recent X-ray crystal structure analysis of nucleic acid polymerases, isoC and K are not recognized as substrates depending on the type of nucleic acid polymerases because they have an amino group instead of the 2-position keto group which is important for interaction with nucleic acid synthetases; and 3) nucleoside derivatives of isoC are chemically unstable. For these reasons, the practical uses of these unnatural base pairs are restricted at present.

On the other hand, the United States groups focused on the hydrophobicity of bases and newly designed hydrophobic base pairs free from hydrogen bonding. First, the group of Kool et al. synthesized adenine and thymine derivatives which lack atoms and functional groups capable of acting as donors or acceptors in hydrogen bonding, and also studied their incorporation into DNA. A hydrophobic base analog corresponding to the adenine derivative is 4-methylbenzimidazole (Z) or 9-methyl-1-H-imidazo[(4,5)-b]pyridine (Q), while a hydrophobic base analog corresponding to the thymine derivative is 2,4-difluorotoluene (F) (FIG. 1c). Although these hydrophobic base pairs have no hydrogen bond between bases to be paired, they are found to be incorporated into DNA in a complementary manner by the Klenow fragment of *E. coli*-derived DNA polymerase I. Other base pairs including A:F, Q:T and Z:T are also shown to be incorporated in a complementary manner [Morales & Kool, 1999].

Subsequently, the group of Romesberg and Schultz et al. synthesized a large number of hydrophobic base pairs and made a comprehensive study of their incorporation into DNA. The results of their study indicate efficient pairing between hydrophobic bases, as exemplified by base pairing between pyrrolopyridine (PP) and C3-methylisocarbostyryl (MICS) (FIG. 1d) [Wu et al., 2000]. However, hydrophobic bases have the property of pairing with each other independently of shape fitting, thus create an additional problem in that even combinations PP:PP and MICS:MICS are also efficiently incorporated into DNA. Moreover, in the case of using the Klenow fragment, elongation does not substantially proceed after incorporation of such base combinations formed without any shape fitting.

Recently, in relation to self-complementary base pairing between 7-azaindoles (7AI) (FIG. 1d), elongation was shown to proceed when using the Klenow fragment in combination with a eukaryotic cell-derived DNA polymerase β [Tae et al., 2001], but such an attempt is not ready for practical use at this stage.

Further studies have been conducted to develop base pairs that have hydrogen-bonding patterns different from those of natural base pairing and that are capable of eliminating base pairing with natural bases by steric hindrance. For example, Ohtsuki et al. (2001) and Hirao et al. (2002) have designed purine derivatives having a bulky substituent at the 6-position, i.e., 2-amino-6-dimethylaminopurine (x) and 2-amino-6-thienylpurine (s), as well as pyridin-2-one (y) having a hydrogen atom at the site complementary to the bulky substituent, and also have studied x:y and s:y base pairing by the efficiency of Klenow fragment mediated incorporation into DNA (FIG. 2). As the results, the incorporation of y opposite x in the template shows low selectivity, whereas the incorporation of y opposite s shows relatively good selectivity and efficiency.

Since the development of the above s-y base pair enables the selective introduction of y into RNA, it will further enable the design of novel functional molecules such as aptamers and ribozymes once y has been modified to have a functional substituent. Thus, there has been a demand for development of such y derivatives.

DISCLOSURE OF THE INVENTION

An object of the present invention is to provide a nucleoside or nucleotide having a 5-substituted-2-oxo(1H)-pyridin-3-yl group as a base.

In the nucleoside or nucleotide of the present invention, the 5-position of the above base is preferably substituted with a substituent selected from the group consisting of the following:

1) a photoreactive group selected from iodine and bromine;
2) an alkenyl group, an alkynyl group or an amino group, or a derivative thereof;
3) biotin or a derivative thereof; and
4) a fluorescent molecule selected from fluorescein, 6-carboxyfluorescein, tetramethyl-6-carboxyrhodamine, and derivatives thereof. The substituent at the 5-position is most preferably an iodine or biotin derivative.

Another object of the present invention is to provide a nucleic acid incorporating the above nucleotide. In one embodiment of the nucleic acid of the present invention, the above nucleotide forms a base pair with a nucleotide having a 6-substituted 2-amino-purin-9-yl group as a base.

Yet another object of the present invention is to provide a method for preparing a nucleic acid incorporating the above nucleotide. The method of the present invention comprises:

effecting transcription, replication or reverse transcription by using, as a template, a nucleic acid containing a nucleotide having a 6-substituted 2-amino-purin-9-yl group as a base, so that the above nucleotide having a 5-substituted-2-oxo(1H)-pyridin-3-yl group as a base is incorporated as a site complementary to the above nucleotide having a 6-substituted 2-amino-purin-9-yl group at a base.

Yet another object of the present invention is to provide a multimer formed between a nucleic acid containing a nucleotide having a 5-substituted-2-oxo(1H)-pyridin-3-yl group as a base and one or more of other molecules (preferably exemplified by biological molecules such as DNA, RNA and protein), wherein the nucleic acid is covalently linked to the molecule via the substituent at the 5-position.

Yet another object of the present invention is to provide a method for forming a multimer between a nucleic acid containing a nucleotide having a 5-substituted-2-oxo(1H)-pyridin-3-yl group as a base and other molecules (more preferably biological molecules), which comprises allowing the nucleic acid to approach the molecules to establish covalent bonding between DNA-DNA, RNA-RNA, DNA-RNA, DNA-protein or RNA-protein via the substituent at the 5-position.

BRIEF DESCRIPTION OF THE DRAWINGS

FIG. 1 shows known natural and artificial base pairs. a) Watson-Crick base pairing. b) Base pairing based on other hydrogen-bonding patterns, reported by Benner et al. c) Base pairing without hydrogen bonding, reported by Kool et al. d) Hydrophobic base pairs, reported by Romesberg and Shultz et al. R denotes sugar.

FIG. 4 shows the structure and UV absorption of the compound according to the present invention, 3-(β-D-ribofuranosyl)-5-iodopyridin-2(1H)-one 5'-triphosphate (5IyTP).

a) 3-(β-D-Ribofuranosyl)-5-iodopyridin-2(1H)-one 5'-triphosphate (5IyTP).

b) UV absorption of 5IyTP in 10 mM phosphate buffer (pH 7). λmax=318 nm.

FIG. 5 shows (a) primers used to prepare template DNA (SEQ ID NOS: 2-7) for site-selective introduction of 5Iy into RNA 9A, along with (b) the sequence of RNA 9A (SEQ ID NO: 1). In (a), each site containing the unnatural base s is expressed as s. In (b), sequence regions of RNA 9A where 5Iy is introduced are underlined.

FIG. 6 shows the site-selective introduction of 5Iy into RNA 9A.

a) Electrophoresis autoradiogram of transcription products obtained in the presence (+) or absence (−) of 0.25 mM 5Iy. The positions where 5Iy is introduced are indicated, along with the full-length position for each product (on the left side).

b) The positions where 5Iy is introduced are marked with solid circles on the secondary structure of RNA 9A (SEQ ID NO: 1).

Figure 7:
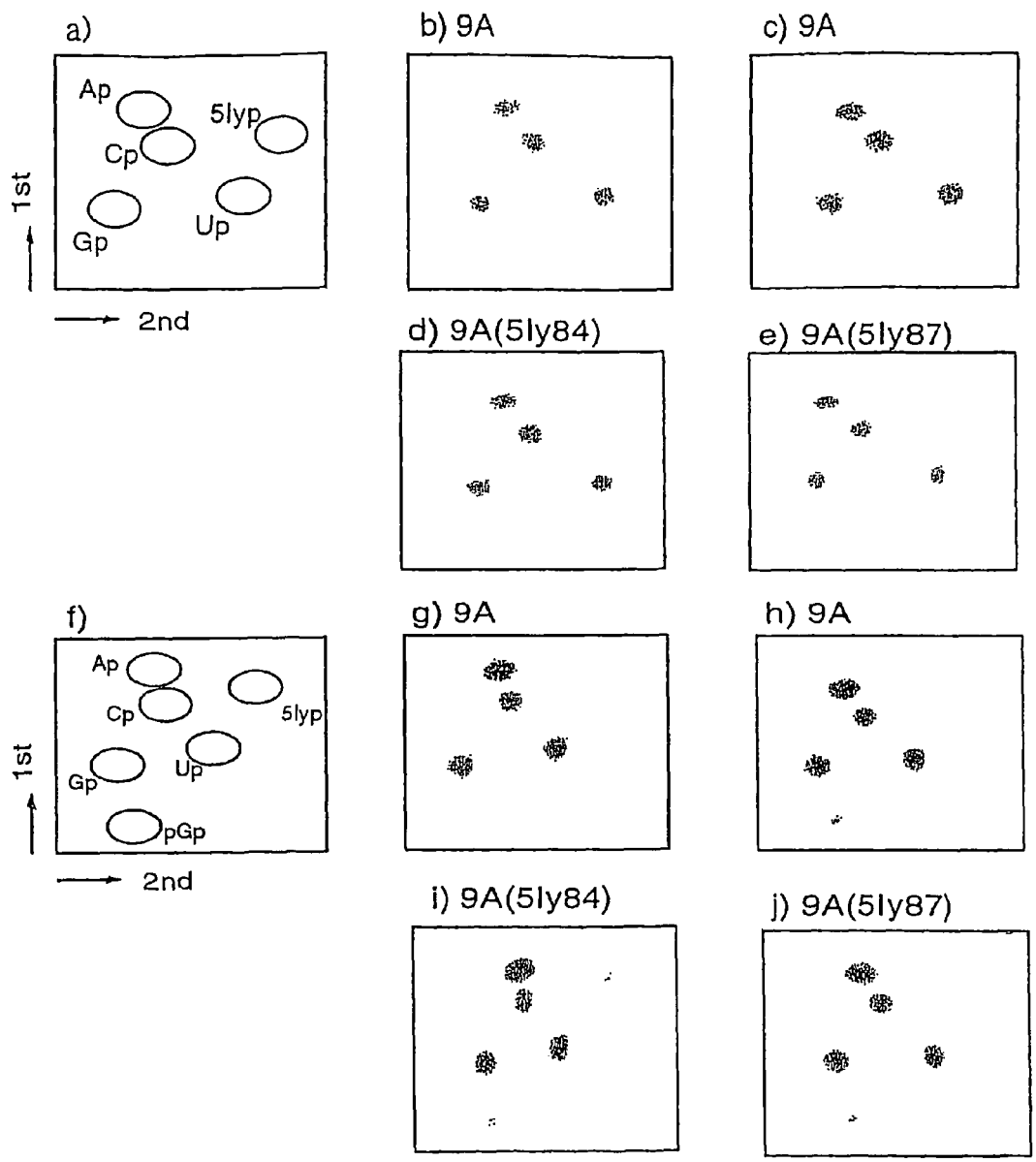

FIG. 7 shows the base composition analysis of transcription products. Reaction products (full-length; see FIG. 6) transcribed in the presence (c-e, h-j) or absence (b, g) of 0.25 mM 5Iy were completely digested with RNase $T_2$ and then analyzed by 2D-TLC. The positions of spots corresponding to the respective bases are shown in a) and f). b-e) Labeled with [α-$^{32}$P]ATP. g-j) Labeled with [α-$^{32}$P]GTP. The quantitative results of the respective spots are shown in Table 1.

Figure 8:
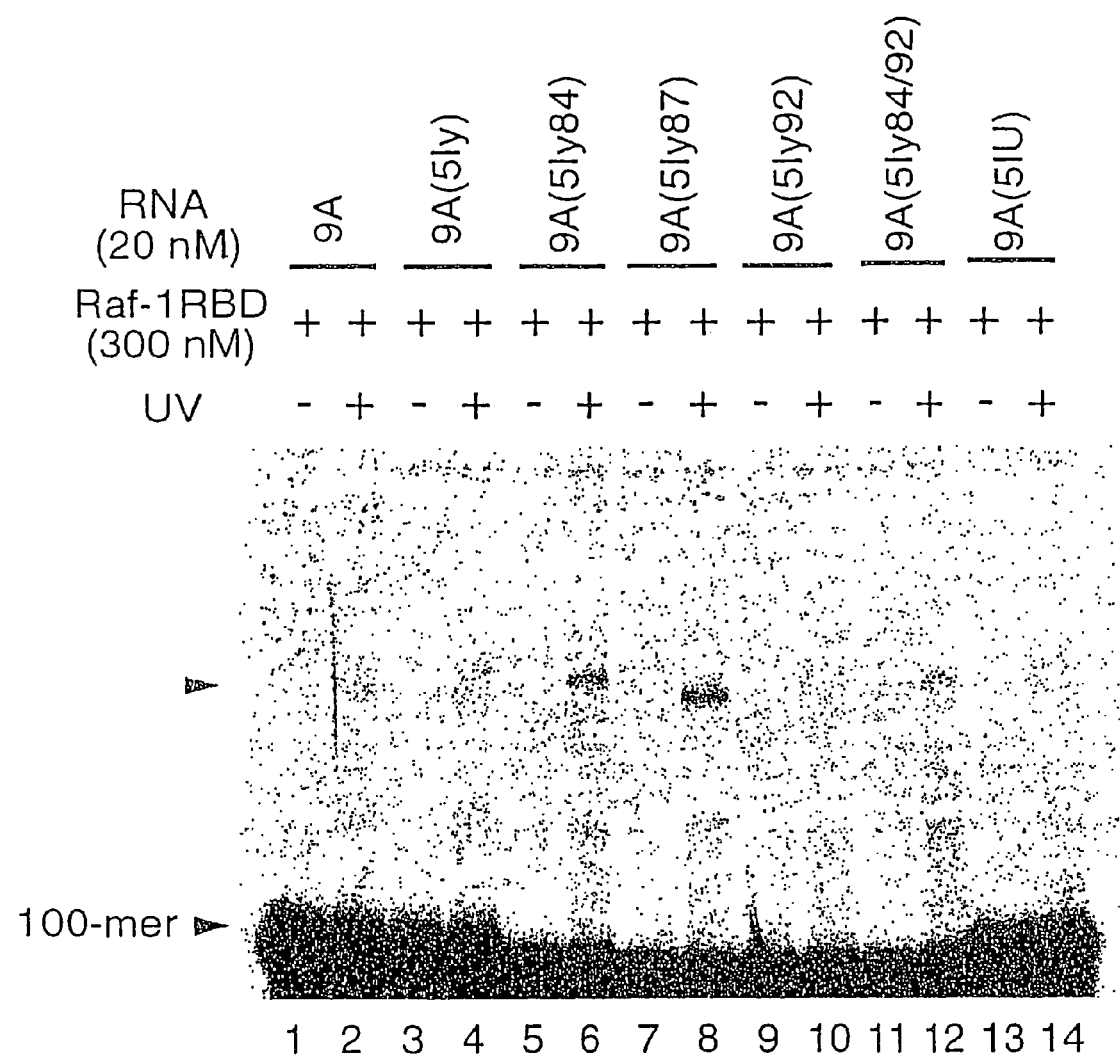

FIG. 8 shows crosslinking reaction in RNA which site-selectively contains 5Iy. Each RNA and GST-RBD were mixed and incubated at 37° C. for 30 minutes, and then irradiated on ice with UV (312 nm) for 1 hour using a UV transilluminator. This figure shows an electrophoresis autoradiogram of the irradiated samples. RNA 9A(5Iy84), 9A(5Iy87), 9A(5Iy92) and 9A(5Iy84/92) were RNA molecules having 5Iy introduced at positions 84, 87, 92, and 84/92, respectively. See Table 2 for 9A(5Iy) and 9A(5IU). The band position of crosslinking products generated by UV irradiation is indicated on the left side.

Figure 9:
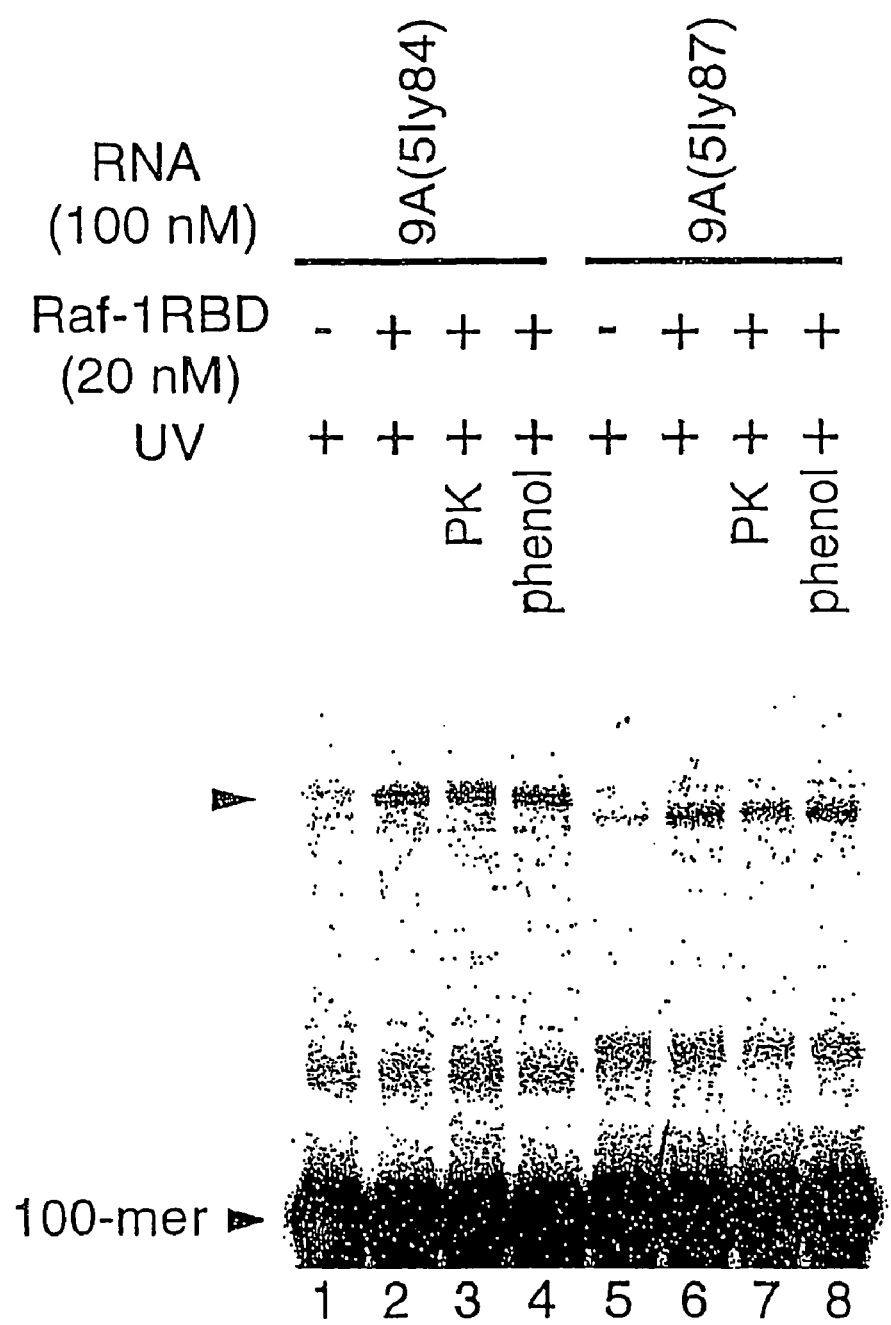

FIG. 9 shows crosslinking reaction in RNA 9A(5Iy84) and 9A(5Iy87). Each RNA was irradiated with UV in the presence (Lanes 2-4, 6-8) or absence (Lanes 1, 5) of GST-RBD. After irradiation, the samples were treated with proteinase K (PK) or extracted with phenol/chloroform (phenol) to remove the protein, indicating that there was no change in the band position of crosslinking reaction products (Lanes 3, 4, 7, 8).

FIG. 10 shows that the crosslinking reaction product (XL) of RNA(5Iy87) is a dimerization product of 9A and binds to 2 molecules of GST-RBD. a-d) Binding between each RNA and GST-RBD was analyzed by gel shift assay. e) The respective sequences of RNA (a-d) are shown (SEQ ID NOS: 1, 11, 12). Regions different from those of the original RNA 9A sequence are in bold type and underlined.

Figure 11:
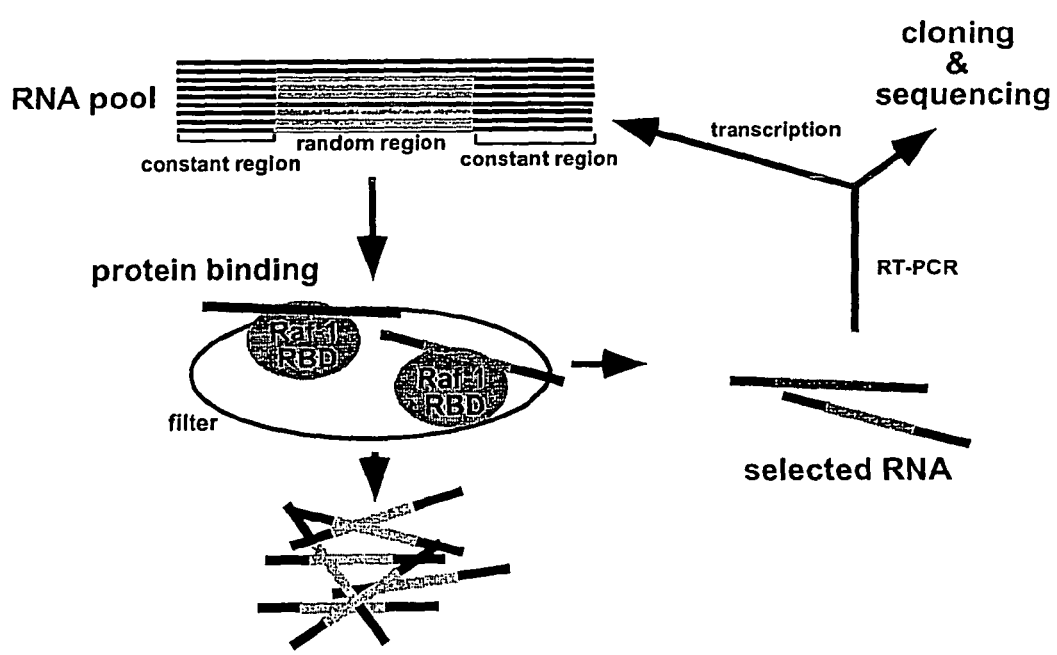

FIG. 11 shows an outline of in vitro selection for RNA aptamers binding to Raf-1 RBD. The selection was accomplished by a filter binding method based on the property of proteins to adsorb to a nitrocellulose filter. An RNA pool containing random sequences is isolated to select RNA bound to Raf-1 RBD, followed by RT-PCR and transcription to amplify the RNA pool for the next round. A series of these procedures is repeated to enrich RNA molecules binding to Raf-1 RBD.

Figure 12:
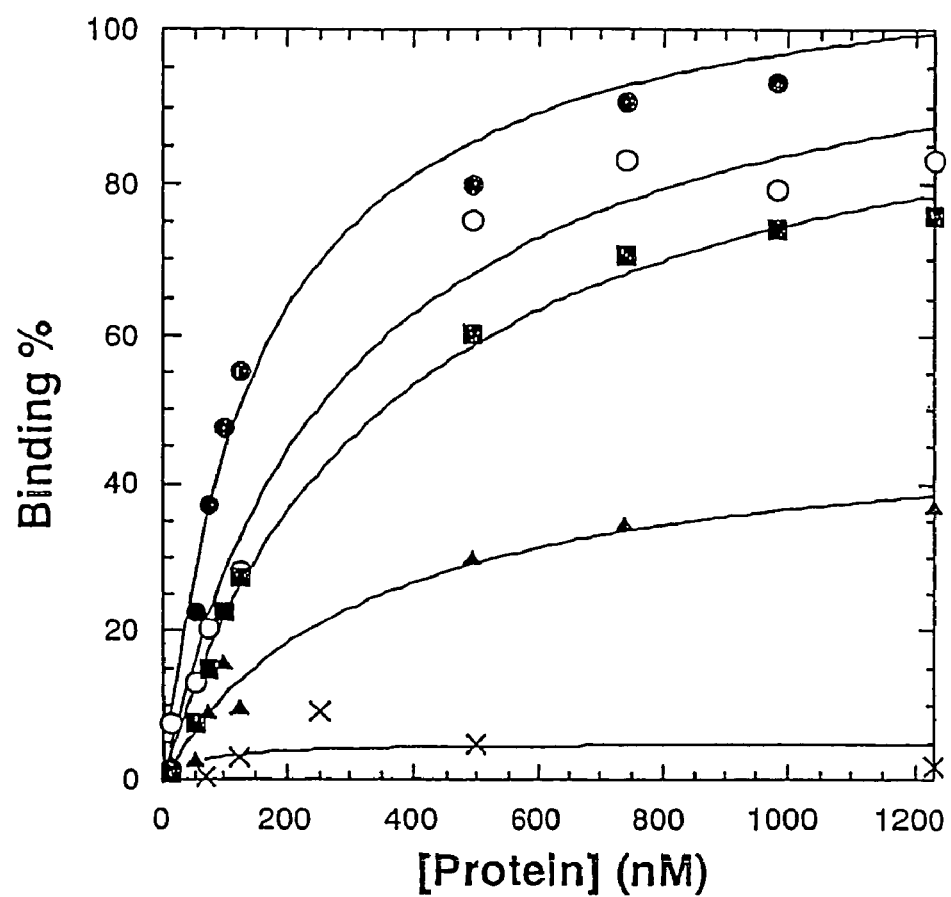

FIG. 12 shows a binding curve between each RNA aptamer and protein. The binding efficiency (Binding %) to various concentrations of protein was determined for each RNA aptamer (2 nM) by a filter binding method and plotted in the figure.

Figure 13:
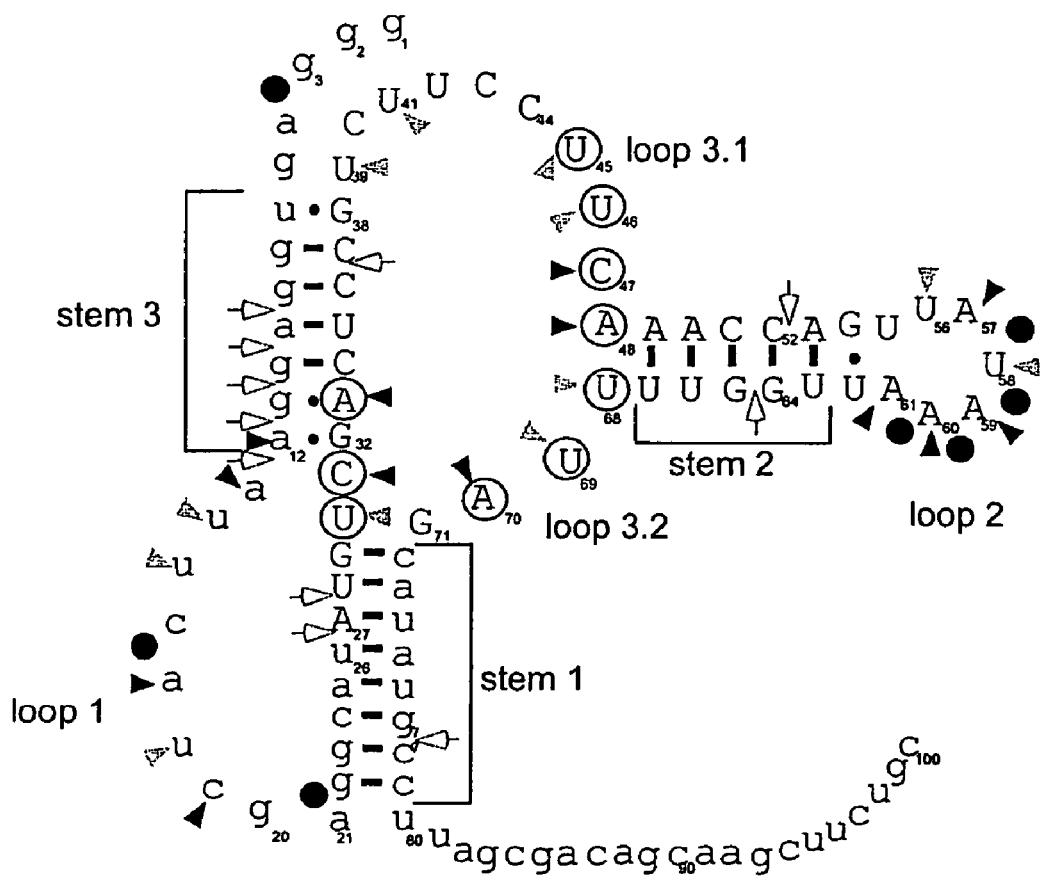

Binding of RNA 9A to Raf-1 GST-RBD: solid circle
Binding of RNA 9A to B-Raf GST-RBD: open circle
Binding of RNA 9A to RGL GST-RBD: x (cross)
Binding of RNA 9B to Raf-1 GST-RBD: solid square
Binding of RNA 21.01 to Raf-1 GST-RBD: solid triangle FIG. 13 shows the secondary structure of RNA 9A (SEQ ID NO: 1). The secondary structure of RNA 9A was estimated by limited hydrolysis with RNase and chemical modification. Constant regions are indicated in lower case letters, while random regions are indicated in upper case letters. The cleavage pattern with RNase and modification patterns with alkylating agents (DMS and CMCT) are separately mapped on the secondary structure. Sequence regions where chemical modification is footprinted in the presence of Raf-1 GST-RBD are marked with open circles.

Figure 14:
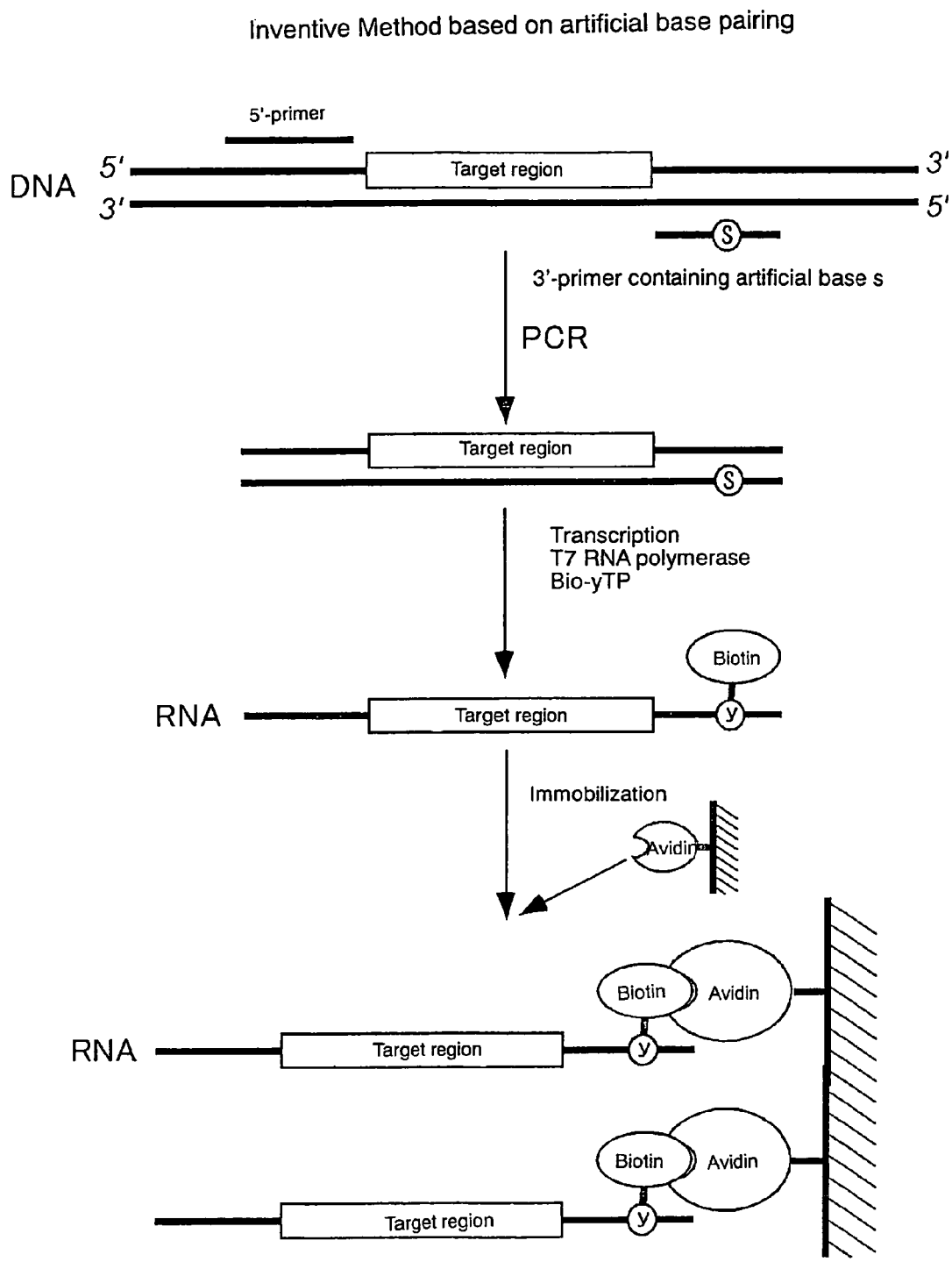

FIG. 14 shows RNA-immobilizing methods based on biotin-avidin interaction. The left panel of the figure illustrates conventional techniques: Conventional Method 1, in which biotin-labeled DNA is attached onto avidinylated carriers and then hybridized with RNA; and Conventional Method 2, in which uridine labeled with biotin at the 5-position is randomly introduced into RNA by transcription and then attached onto avidinylated carriers (FIG. 14). The right panel of the figure illustrates the method of the present invention, in which the biotin-labeled fifth base is introduced by transcription at a specific site in RNA through artificial base pairing.

Figure 15:
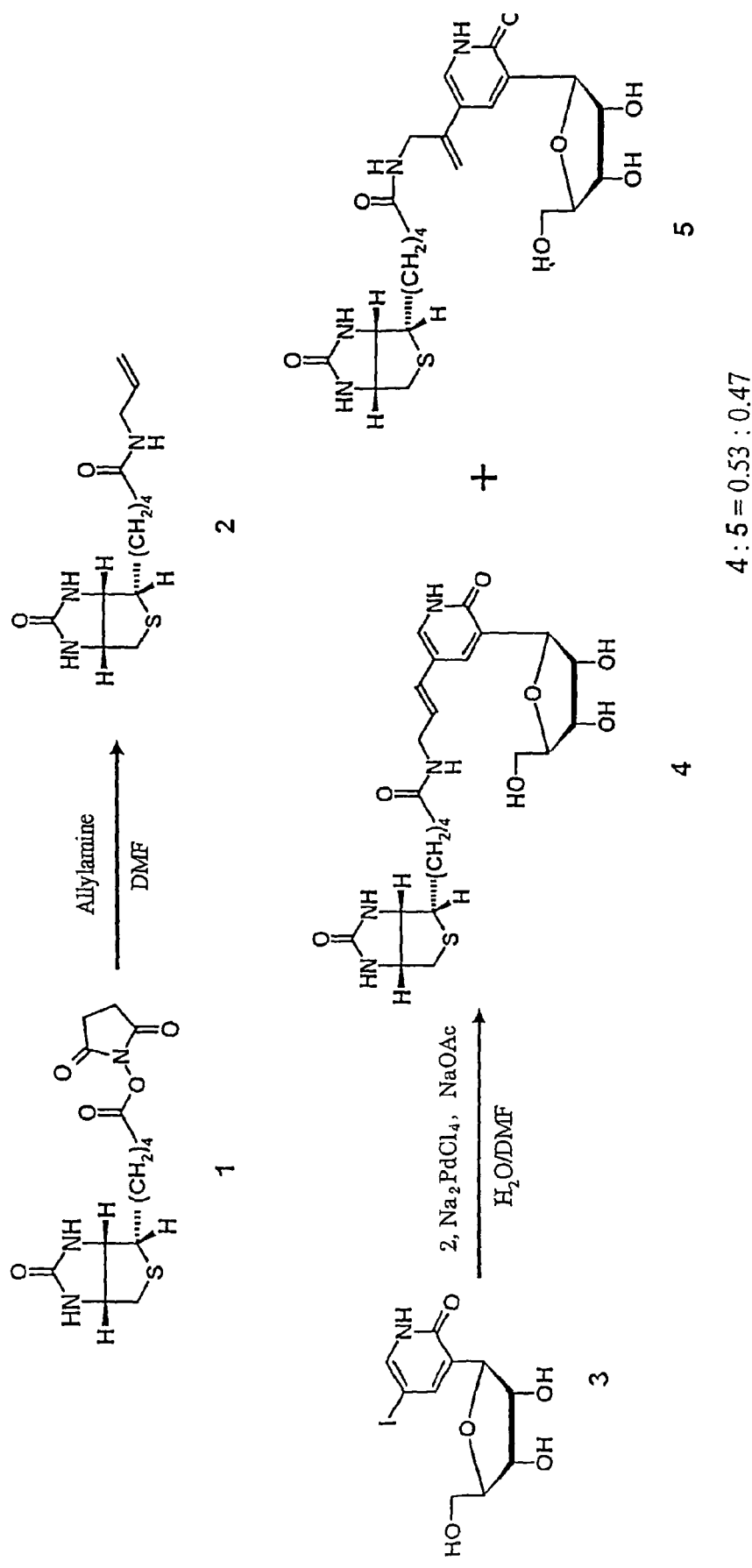

FIG. 15 shows the synthesis of the y derivative of the present invention, which is labeled with biotin via an ethylenic linker.

Figure 16:
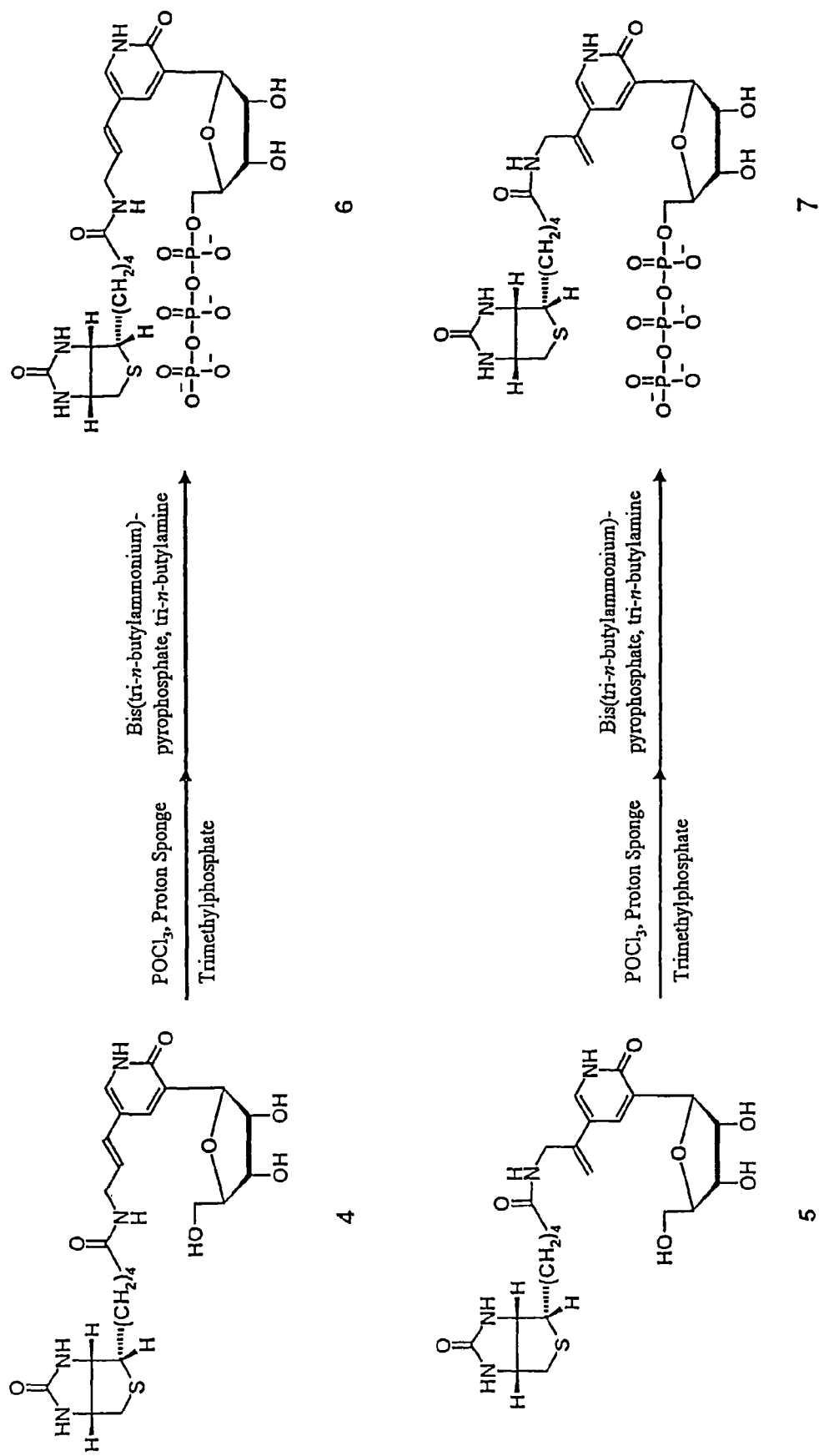

FIG. 16 shows the triphosphorylation of the y derivative of the present invention, which is labeled with biotin via an ethylenic linker.

Figure 17:
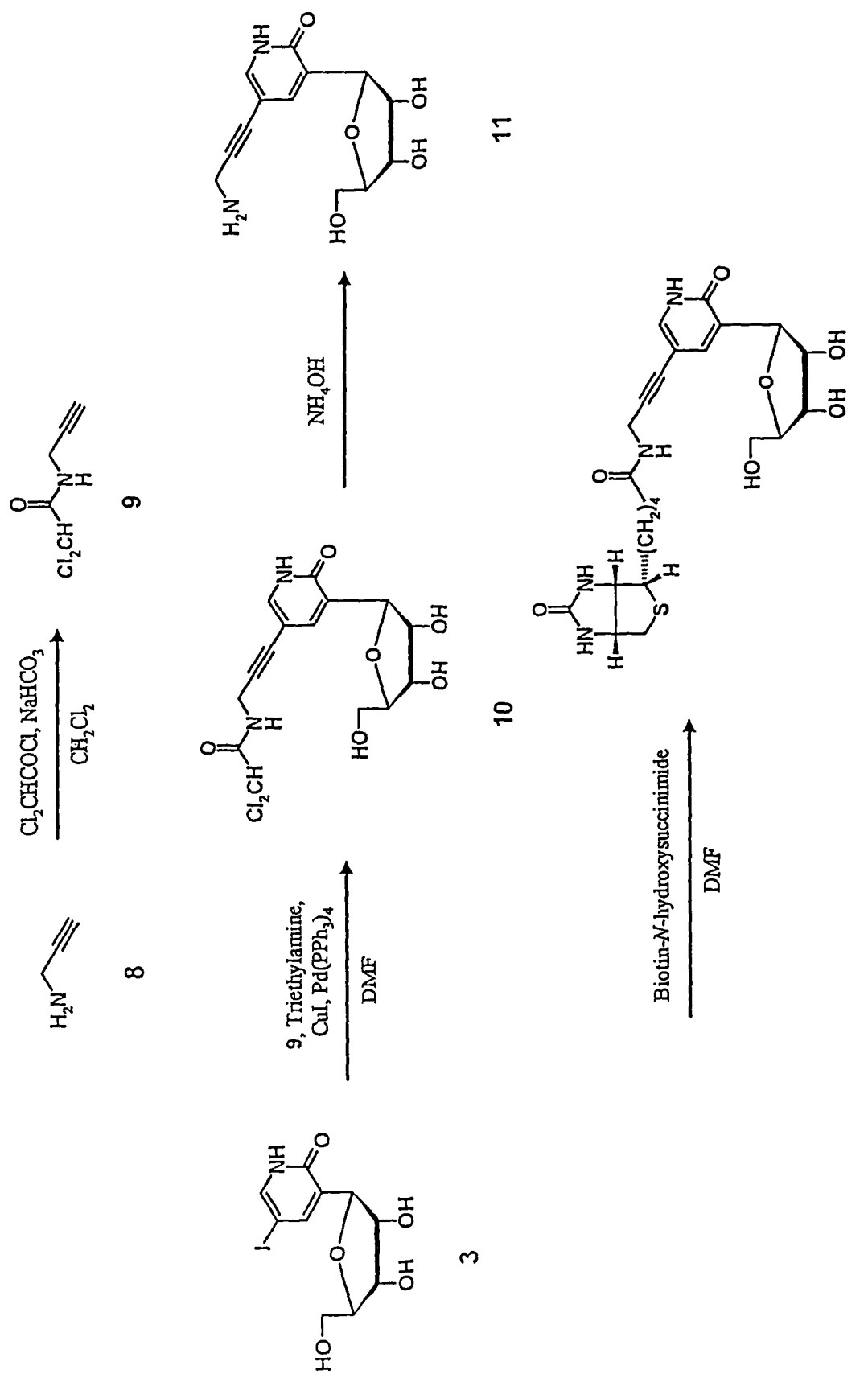

FIG. 17 shows the synthesis of the y derivative of the present invention, which is labeled with biotin via an acetylenic linker.

Figure 18:
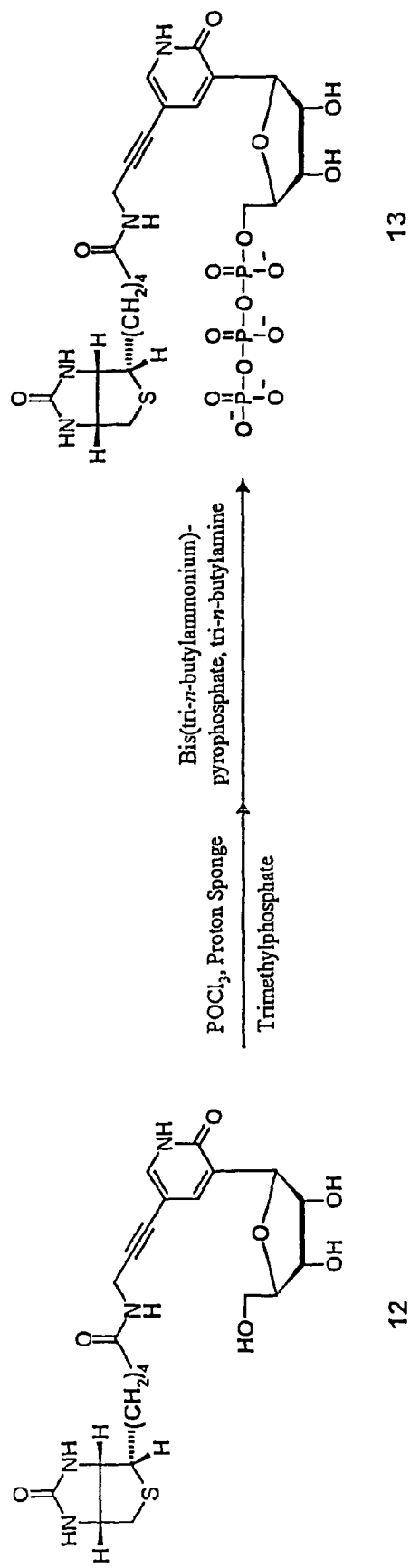

FIG. 18 shows the triphosphorylation of the y derivative of the present invention, which is labeled with biotin via an acetylenic linker.

Figure 19:
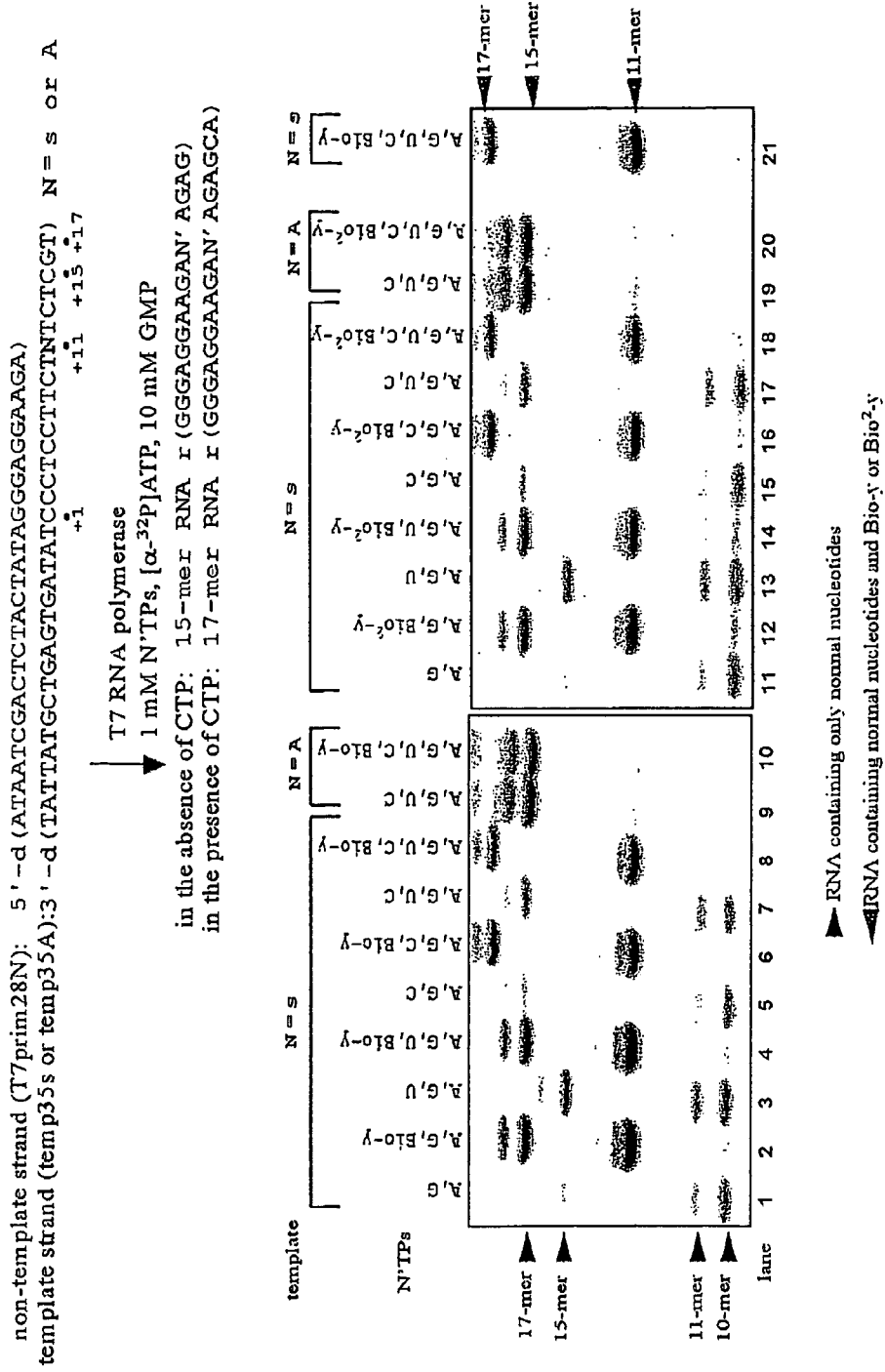

FIG. 19 shows the site-selective introduction of Bio-yTP (Compound 6) and $Bio^2$-yTP (Compound 13) into RNA (SEQ ID NOS: 10, 8, 13, 14). This figure shows an electrophoresis autoradiogram of transcription products obtained in the presence (+) or absence (−) of 1 mM Bio-yTP or $Bio^2$-yTP. The lengths of products introduced with and without Bio-yTP or $Bio^2$-yTP are indicated with arrows on the right and left sides, respectively.

BEST MODE FOR CARRYING OUT THE INVENTION

In the case of using unnatural base pairing s:y, misincorporation of U showed negligible selectivity, which indicated that s:y base pairing could be used for a new interaction between codon and anticodon when y was introduced at a specific site in mRNA [Hirao et al., 2002]. The inventors of the present invention have addressed site-selective introduction of a 5-substituted y derivative into RNA to generate RNA molecules having new functions, and they finally have arrived at the present invention.

Nucleosides or Nucleotides Having a
5-substituted-2-oxo(1H)-pyridin-3-yl Group as a
Base The present invention provides a nucleoside or nucleotide having a 5-substituted-2-oxo(1H)-pyridin-3-yl group as a base. The inventive nucleoside or nucleotide having a 5-substituted pyridine base is advantageous in that it is less likely to cause unwanted base-base interference (e.g., steric hindrance and unwanted binding observed during base pairing) when compared to a nucleoside or nucleotide having a substituent at the 1-, 2- or 6-position of the pyridine base.

As used herein, the term "nucleoside" is intended to mean a glycoside compound formed through glycosidic linking between a nucleic acid base and a reducing group of a sugar. It should be noted that the term "nucleic acid base" is intended to encompass adenine, guanine, cytosine, thymine, uracil, and also derivatives thereof. The type of the above "derivative" is not limited in any way. Specific examples include bases equivalent to a 5-substituted-2-oxo(1H)-pyridin-3-yl group and bases equivalent to a 2-amino-6-(2-thienyl)purin-9-yl group. The term "nucleotide" refers to a compound in which the sugar moiety of the above nucleoside forms an ester with phosphoric acid, more preferably a mono-, di- or triphosphate ester. The sugar moiety of such a nucleoside or nucleotide may be ribofuranosyl, 2'-deoxyribofuranosyl, or 2'-substituted ribofuranosyl having a substituent (e.g., halogen) at the 2'-position. Likewise, the phosphoric acid moiety may be thiophosphoric acid. Namely, the sugar and phosphoric acid moieties may be in the same form as found in known nucleosides, nucleotides, or derivatives thereof. A ribonucleotide whose sugar moiety is ribofuranosyl can be used as a member constituting RNA, while a deoxyribonucleotide whose sugar moiety is deoxyribofuranosyl can be used as a member constituting DNA.

In the nucleoside or nucleotide of the present invention, the 5-position of the above base is preferably substituted with a substituent selected from the group consisting of the following:

1) a photoreactive group selected from iodine and bromine;
2) an alkenyl group, an alkynyl group or an amino group, or a derivative thereof;
3) biotin or a derivative thereof; and
4) a fluorescent molecule selected from fluorescein, 6-carboxyfluorescein, tetramethyl-6-carboxyrhodamine, and derivatives thereof.

1) A photoreactive group selected from iodine and bromine will generate radicals upon light irradiation and produce covalent bonding between adjacent molecules. In the case of iodine (5-iodo y), without being limited thereto, light irradiation may preferably be accomplished by UV irradiation at around 318 nm for about 1 hour.

Without being limited thereto, the substituent at the 5-position is most preferably iodine. The structural formula of a 3-(β-D-ribofuranosyl)-5-iodopyridin-2(1H)-one 5'-triphosphate derivative (5IyTP) is shown in FIG. 4a).

2) The base in the nucleoside or nucleotide of the present invention may have an alkenyl group, an alkynyl group or an amino group, or a derivative thereof as a substituent at the 5-position.

These alkenyl, alkynyl and amino groups, as well as derivatives thereof are helpful in hydrophobic or hydrophilic interaction with other molecules, for example, to enhance interaction between aptamers and their target molecules. In the case of ribozymes, these groups are also helpful to create a new active site. Further, a derivative of an amino group can be used as a synthetic intermediate to prepare a derivative labeled with biotin or a fluorescent dye.

The alkenyl or alkynyl group preferably contains 2 to 5 carbon atoms, and more preferably 2 to 3 carbon atoms. Examples of their derivatives include —C≡CC$_6$H$_5$, —C≡CCH$_2$NH$_2$ and —CH=CH—CH$_2$—NH$_2$. Preferred is —C≡CC$_6$H$_5$ (a 2-phenylethynyl group).

3) Biotin is also called Coenzyme R and is a member of vitamins B. Biotin is known to specifically bind to and form a conjugate with avidin (a glycoprotein contained in albumen). Thus, the inventive nucleoside or nucleotide having biotin as a substituent at the 5-position will specifically bind to avidin protein. This means that a nucleic acid containing the biotin-labeled inventive nucleoside or nucleotide can be attached to and hence immobilized on avidin-bound carriers. If nucleic acids (e.g., aptamers) binding to specific molecules are immobilized, such immobilized nucleic acids can be used for detection and isolation of specific substances or used as diagnostic reagents, by way of example.

A conventional technique known for labeling nucleic acids with biotin involves preparing biotin-labeled short DNA through chemical synthesis, attaching the DNA onto avidinylated carriers, and hybridizing the immobilized DNA with a complementary nucleic acid (FIG. 14, Conventional Method 1). This method requires DNA synthesis and hybridization, which make the procedure complicated. In addition, the efficiency of nucleic acid immobilization depends on hybridization between biotin-labeled short DNA and a complementary sequence containing a target sequence, rather than on biotin-avidin binding.

Another conventional technique is also known in which uridine labeled with biotin at the 5-position is used to randomly introduce biotin into RNA (opposite A in template DNA) by transcription, and then attached onto avidinylated carriers (FIG. 14, Conventional Method 2). In relation to this method, substrates of biotin-labeled uridine (U) (as well as derivatives of A, G and C) are commercially available from the following companies: Roche/Boehringer Manheim, Clontech, Enzo and PerkinElmer. However, this method suffers from a fundamental problem in that the biotin-labeled uridine is "randomly" introduced into RNA opposite A in template DNA. This may lead to the functional loss of the immobilized RNA and/or a reduction in the immobilization efficiency.

In contrast to these conventional techniques, if the biotin-labeled fifth base can be introduced by transcription at a specific site in a nucleic acid through artificial base pairing, it significantly facilitates the biotinylation of nucleic acids and hence the immobilization of nucleic acids. The present invention achieves these goals by using an artificial base pair s-y. To introduce biotin as a substituent at the 5-position of the nucleoside or nucleotide of the present invention, biotin may be introduced directly, but preferably via a linker selected from an aminoalkyl group, an aminoalkenyl group and an aminoalkynyl group. For example, in Examples 11-15 of the present invention (FIGS. 15-18), biotin was introduced at the 5-position of y via either of two linkers, ethylenic or acetylenic. As used herein, the term "biotin derivative" is intended to also include biotin modified to have a linker for introduction into nucleosides or nucleotides.

4) In a case where the 5-position substituent is a fluorescent molecule selected from fluorescein, 6-carboxyfluorescein, tetramethyl-6-carboxyrhodamine and derivatives thereof, nucleic acids containing the nucleotide of the present invention may be detected in a manner depending on the type of fluorescent molecule. Thus, a nucleic acid containing the inventive nucleotide having a fluorescent molecule at the 5-position can be used as a labeled nucleic acid probe to detect substances interacting with the nucleic acid.

Without being limited thereto, fluorescein has an absorption peak wavelength of 513 nm and a fluorescence peak wavelength of 532 nm. Likewise, 6-carboxyfluorescein has an absorption peak wavelength of 495 nm and a fluorescence peak wavelength of 521 nm, while tetramethyl-6-carboxyrhodamine has an absorption peak wavelength of 555 nm and a fluorescence peak wavelength of 580 nm. Since these substances have fluorescent colors different from each other, they can also be used in multiple staining.

The inventive nucleoside or nucleotide having a 5-substituted-2-oxo(1H)-pyridin-3-yl group as a base may be synthesized in any manner, depending on the type of substituent. By way of example, as described in Example 1 below, 3-(β-D-ribofuranosyl)-pyridin-2(1H)-one may first be introduced with a substituent at the 5-position and then introduced with triphosphoric acid. Alternatively, 3-(β-D-ribofuranosyl)-pyridin-2(1H)-one may first be introduced with triphosphoric acid and then introduced with a substituent. In the case of introducing a bulky group such as an alkenyl group, an alkynyl group, an amino group, or a derivative thereof as mentioned in 2), a photoreactive group (e.g., iodo) may first be introduced to activate the base prior to substitution. Reaction conditions used for introducing these substituents may be determined with reference to cases where the substituents are introduced into pyridine.

Nucleic Acids Incorporating the Nucleosides or Nucleotides of the Present Invention The present invention provides a nucleic acid that incorporates a nucleotide having a 5-substituted-2-oxo(1H)-pyridin-3-yl group as a base. The nucleic acid of the present invention encompasses single-stranded or double-stranded RNA or DNA. The double-stranded nucleic acid may be DNA/DNA, RNA/RNA, or DNA/RNA. DNA also includes cDNA obtained by reverse transcription using RNA as a template. Alternatively, the nucleic acid may form a triplex, a quadruplex, etc.

Figure 2:
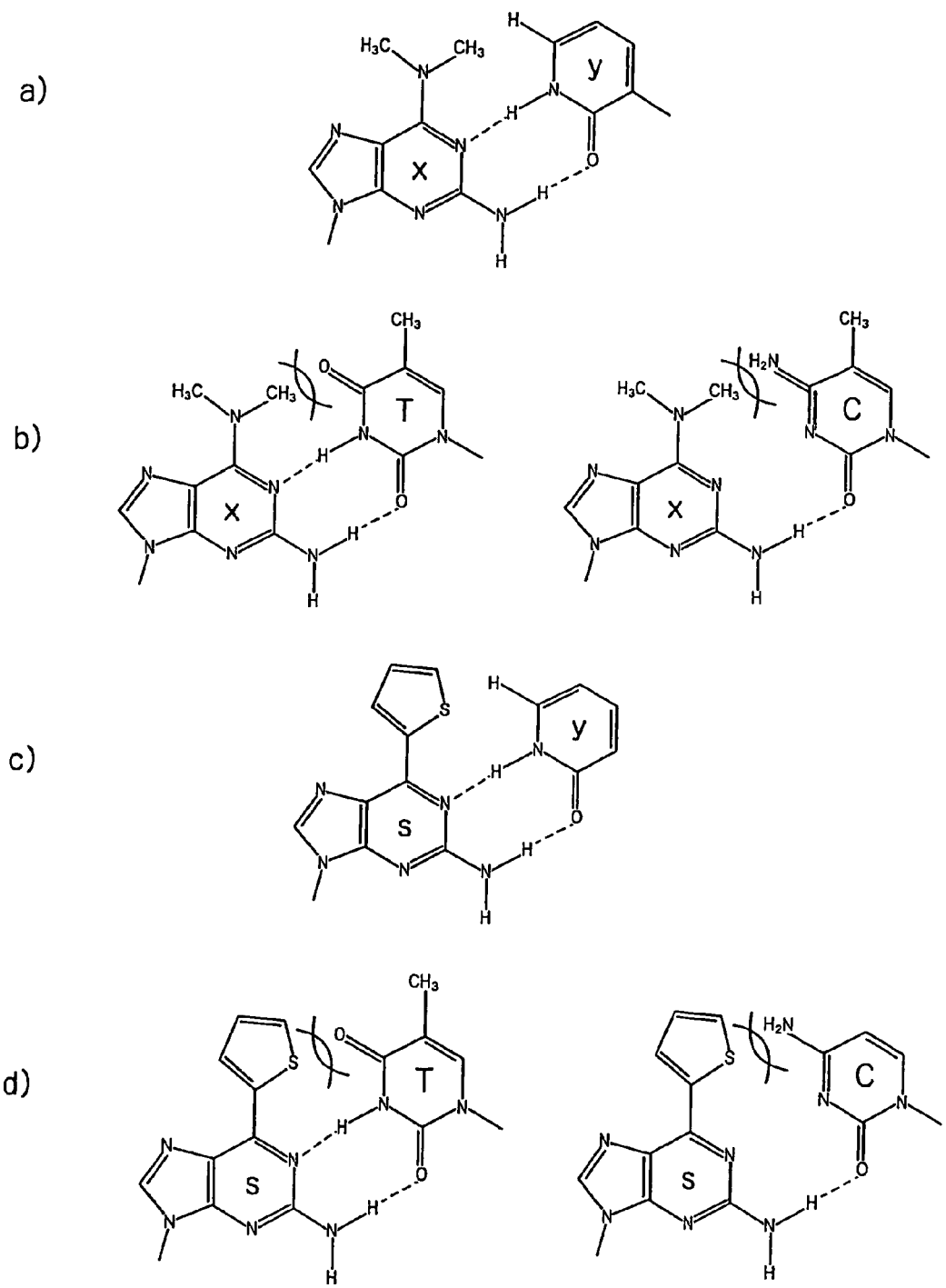
FIG. 2 shows artificial base pairs designed based on differences in hydrogen-bonding patterns and the concept of steric hindrance (shape fitting). a) Base pairing between 2-amino-6-dimethylaminopurine (x) and pyridin-2-one (y). b) Base pairing between x and a natural pyrimidine base. c) Base pairing between 2-amino-6-thienylpurine (s) and y. d) Base pairing between s and a natural pyrimidine base.

The nucleoside or nucleotide of the present invention can form a base pair with a nucleoside or nucleotide having a 6-substituted 2-amino-purin-9-yl group as a base. As in the case of y and s (a 2-amino-6-(2-thienyl)purin-9-yl group) shown in FIG. 2c, the 5-substituted-2-oxo(1H)-pyridin-3-yl group of the present invention forms two hydrogen bonds with the 6-substituted 2-amino-purin-9-yl group. The 6-substituted 2-amino-purin-9-yl group is preferably a 2-amino-6-(2-thienyl)purin-9-yl group (s) or a 2-amino-6-(dimethylamino)purin-9-yl group (x), and more preferably a 2-amino-6-(2-thienyl)purin-9-yl group (s).

The 5-substituted-2-oxo(1H)-pyridin-3-yl group of the present invention cannot form any base pair with natural purine bases A (adenine) and G (guanine) in terms of its stereostructure. Likewise, the 6-substituted 2-amino-purin-9-yl group cannot form any base pair with natural T (thymine), U (uracil) and C (cytosine) due to steric hindrance. Thus, the 5-substituted-2-oxo(1H)-pyridin-3-yl group of the present invention can specifically form a base pair with the 6-substituted 2-amino-purin-9-yl group.

The nucleic acid of the present invention therefore includes an embodiment wherein base pairs are formed between a nucleotide having the 5-substituted-2-oxo(1H)-pyridin-3-yl group as a base and a nucleotide having the 6-substituted 2-amino-purin-9-yl group as a base. The 6-substituted 2-amino-purin-9-yl group is preferably a 2-amino-6-(2-thienyl)purin-9-yl group or a 2-amino-6-(dimethylamino)purin-9-yl group.

The inventive nucleotide having the 5-substituted-2-oxo (1H)-pyridin-3-yl group as a base can be incorporated into nucleic acids such as DNA or RNA through transcription, replication or reverse transcription reaction.

Without being limited thereto, a nucleic acid incorporating the nucleotide of the present invention may be prepared by a method comprising:

effecting transcription, replication or reverse transcription by using, as a template, a nucleic acid containing a nucleotide having a 6-substituted 2-amino-purin-9-yl group as a base, so that the nucleic acid of the present invention is incorporated at a site complementary to the above nucleotide having a 6-substituted 2-amino-purin-9-yl group as a base. Alternatively, the nucleotide of the present invention may be incorporated into DNA or RNA through chemical synthesis, as in the case of nucleosides or nucleotides having natural bases.

For example, in a case where a uridine (U) derivative having an iodine atom at the 5-position, i.e., 5-iodo U (5IU) is introduced into RNA through transcription reaction, the transcription reaction must be performed at varying UTP/5IUTP ratios to randomly replace U positions by 5IU, or alternatively, 5IUTP must be used alone instead of UTP in the transcription reaction to replace all U positions by 5IU. In this case, the introduction of 5IU may cause some change in the higher-order structure of RNA and/or will impair the functions of RNA [Jensen et al., 1995]. In contrast, the 5-substituted-2-oxo(1H)-pyridin-3-yl group of the present invention specifically forms a base pair with a 6-substituted 2-amino-purin-9-yl group. This enables the site-selective introduction of a nucleoside or nucleotide having a 5-substituted-2-oxo (1H)-pyridin-3-yl group as a base when DNA or RNA having a 6-substituted-2-amino-purin-9-yl group(s) introduced at a desired position(s) is used as a template, by transcription, replication or reverse transcription.

These transcription, replication and reverse transcription may be accomplished according to known techniques. Without being limited thereto, for example, it is possible to use T7 RNA polymerase (Takara or other suppliers) for transcription, Klenow fragment (KF) for replication, and AMV Reverse Transcriptase XL (AMV-RT, Life Science) for reverse transcription. In order to avoid removal of a 6-substituted 2-amino-purin-9-yl group(s) during the reaction, the replication may also be accomplished, for example, by using Taq DNA polymerase (Takara Taq™) lacking 3'→5' exonuclease activity to effect PCR amplification of template DNA with an s-containing primer.

A nucleotide having a 6-substituted 2-amino-purin-9-yl group as a base may be synthesized in a known manner, for example, as described in Fujiwara et al., 2001.

The nucleic acid incorporating the nucleotide of the present invention may be used as antisense DNA or RNA, a ribozyme or an aptamer. The term "antisense DNA or RNA" refers to DNA or RNA capable of inhibiting the expression of a specific gene. It was named to mean that such DNA or RNA is complementary to the full-length or partial sequence of a target gene sequence (sense strand). Antisense DNA or RNA may be used as a tool for artificial regulation of gene expression. Because of containing unnatural bases, such antisense DNA or RNA incorporating the nucleotide of the present invention can be designed to have a different complementarity to a target when compared to the case of using natural bases only. The term "ribozyme" is a generic name for catalysts composed of RNA and falls within the scope of antisense RNA in a broad sense. The term "aptamer" refers to an in vitro-selected nucleic acid having the ability to bind to a specific molecule.

For example, in vitro-selected aptamers containing a 5-substituted 2-oxo(1H)-pyridin-3-yl group enable the creation of RNA molecules having new functions, e.g., the ability to crosslink with a target protein.

For this purpose, a template DNA pool may first be amplified by PCR, e.g., using an s-containing primer and then transcribed to prepare an RNA pool containing 5Iy at a 3'-terminal specific site(s). In vitro selection may be performed on this RNA pool to obtain a specific aptamer, as measured by the presence of photo-crosslinking. Since 5Iy is located on the 3'-side in the resulting RNA aptamer, it is less likely to adversely affect the efficiency of reverse transcription during the selection. The selection may further be modified such that a hydrophobic substituent is introduced to enhance hydrophobic-hydrophobic binding between target substance and aptamer.

Preparation of nucleic acid molecules having biotin as a substituent at the 5-position may also be accomplished by transcription reaction. Such molecules are available for use in techniques based on biotin-avidin interaction, e.g., RNA immobilization and multimerization. As described later in Example 16, the inventors of the present invention prepared template DNA containing an artificial base s and performed transcription reaction on the template DNA, thus succeeding in the site-specific incorporation of biotinylated nucleosides or nucleotides into the resulting transcription product.

In Example 16, when a 17-mer sequence was introduced with one base having biotin as the 5-position substituent of the present invention, the synthesis efficiency of this case was about 50% as compared to the efficiency in natural base pairs (GC or AT base pairs) (FIG. 19).

There is another report in which a fluorescent molecule is introduced into an RNA aptamer for use as an analyte [Jhaveri et al., 2000; Yamamoto et al., 2000; Fang et al., 2001].

Previous cases reported of in vitro selection employed the following nucleosides as modified bases: fluorescein-12-uracil (F-12-U) [Jhaveri et al., 2000], 5-(1-pentynyl)uracil [Latham et al., 1994], 5-(3"-aminopropynyl)uracil [Battersby et al., 1999], 5-iodouracil (5IU) [Jensen et al., 1995] and 5-bromouracil (5BrU) [Golden., et al., 2000]. In all of these cases, however, replacement between modified base and natural base (T or U) starts at the stage of preparing a DNA or RNA pool. In contrast, the present invention employs specific base pairing between 5-substituted-2-oxo(1H)-pyridin-3-yl and 6-substituted 2-amino-purin-9-yl groups, thus enabling the nucleotide of the present invention to be site-selectively incorporated into RNA via a single step of transcription reaction. If it is possible to freely prepare RNAs composed of 5 types of bases including the unnatural base of the present invention, such RNAs have great utility and versatility.

The DNA or RNA incorporating the nucleotide of the present invention may also encode all or part of a protein or peptide.

Multimers Formed Between Nucleic Acids Containing the Nucleotide of the Present Invention and Other Molecules (e.g., Nucleic Acids, Proteins)

Further, the present invention aims to provide a multimer formed between a nucleic acid containing a nucleotide having a 5-substituted-2-oxo(1H)-pyridin-3-yl group as a base and one or more of other molecules (preferably exemplified by biological molecules such as DNA, RNA and protein), wherein the nucleic acid is covalently linked to the molecule via the substituent at the 5-position.

Furthermore, the present invention aims to provide a method for forming a multimer among a nucleic acid containing a nucleotide having a 5-substituted-2-oxo(1H)-pyridin-3-yl group as a base and other molecules (more preferably biological molecules), which comprises allowing the nucleic acid to approach the molecules to establish covalent bonding between DNA-DNA, RNA-RNA, DNA-RNA, DNA-protein or RNA-protein via the substituent at the 5-position.

As described above, the 5-substituted-2-oxo(1H)-pyridin-3-yl group in the nucleoside or nucleotide of the present invention may form covalent bonding with other molecules located adjacent thereto in a manner depending on the type of substituent at the 5-position.

More specifically, in a case where the 5-position substituent is 1) a photoreactive group selected from iodine and bromine, the nucleic acid of the present invention may be irradiated at a wavelength suitable for the type of reactive group to form covalent bonding with other molecules located adjacent thereto. For example, in the Examples section below, 5Iy was site-selectively introduced into the anti-(Raf-1) aptamer (RNA 9A) obtained in Reference Example 1, followed by crosslinking reaction in the presence of a target protein (Raf-1 RBD) to analyze the effectiveness of the unnatural base of the present invention. Within the 3'-terminal region of RNA 9A which had been found to be not important for interaction with RBD, C84, C87 and A92, each being flanked by two purine bases, were selected as sites for 5Iy introduction in order to minimize changes in the higher-order structure of RNA and/or formation of pyrimidine dimmers, etc. RNAs having 5Iy at these respective sites were then irradiated in the presence of Raf-1 RBD fused N-terminally to GST (glutathione transferase) (GST-RBD) to cause crosslinking reaction. As a result, the RNAs containing 5Iy at residue 84 or 87 were found to form RNA-RNA dimers through crosslinking reaction. Since GST protein dimerizes in solution, GST-RBD will also dimerize in solution. When binding to Raf-1 RBD, RNA 9A molecules will approach each other at the 5Iy-containing sequence region to cause crosslinking between RNA molecules. This result indicates that 5Iy can be used for analysis of RNA-RNA interactions. In the present invention, the statement where a nucleic acid having a 5-substituted-2-oxo(1H)-pyridin-3-yl group as a base and other molecules approach each other is intended to mean that the 5-position substituent and other molecules are located in close enough physical proximity to form covalent bonding.

In the present invention, covalent bonding, which is stronger than other bonding (e.g., hydrogen bonding), is formed between the 5-position substituents to cause crosslinking, thus enabling separation and purification, etc. The present invention also enables a more direct analysis of interactions between nucleic acids and other molecules. Analysis of crosslinking products may be accomplished in a known manner, e.g., by gel shift assay, chromatograph, mass spectrum, etc. The nucleic acid of the present invention and other molecules can form not only dimers, but also trimers or higher multimers.

Alternatively, it is also possible to monitor interactions between proteins attached to DNA or RNA having the 5-substituted-2-oxo(1H)-pyridin-3-yl group of the present invention as a base. For example, in the Example section below, dimerization between RNA molecules was observed in RNA 9A (an RNA aptamer binding to Raf-1 RBD) when site-selectively introduced with the nucleoside or nucleotide of the present invention. This is because GST-RBD used in the Examples section would dimerize in solution and hence RNA 9A molecules, upon binding to the RBD moiety, would approach each other to cause crosslinking between RNA molecules. GST protein is likely to dimerize and is actually used as a domain for protein dimerization. Thus, when crosslinking products are analyzed using the crosslinking reaction of DNA or RNA having the 5-substituted-2-oxo(1H)-pyridin-3-yl group of the present invention as a base, it is also possible to analyze interactions between proteins attached to the DNA or RNA.

Alternatively, the present invention enables the enhancement of nucleic acid molecule/protein interactions, thus providing a tool useful for achieving aptamer-induced inhibition of target protein activity or analyzing nucleic acid/protein interactions, etc. For example, conventional aptamers capable of inhibiting target protein activity do not covalently bind to their target proteins and hence cannot completely inhibit the activity of the proteins. In contrast, 5Iy-containing aptamers can be used to completely inhibit the activity of their target proteins by being covalently bound to the target proteins through light irradiation.

EXAMPLES

The present invention will now be further described in the following examples, which are not intended to limit the technical scope of the invention. Based on the detailed description, various changes and modifications will be apparent to those skilled in the art, and such changes and modifications fall within the technical scope of the invention.

Example 1

Figure 3:
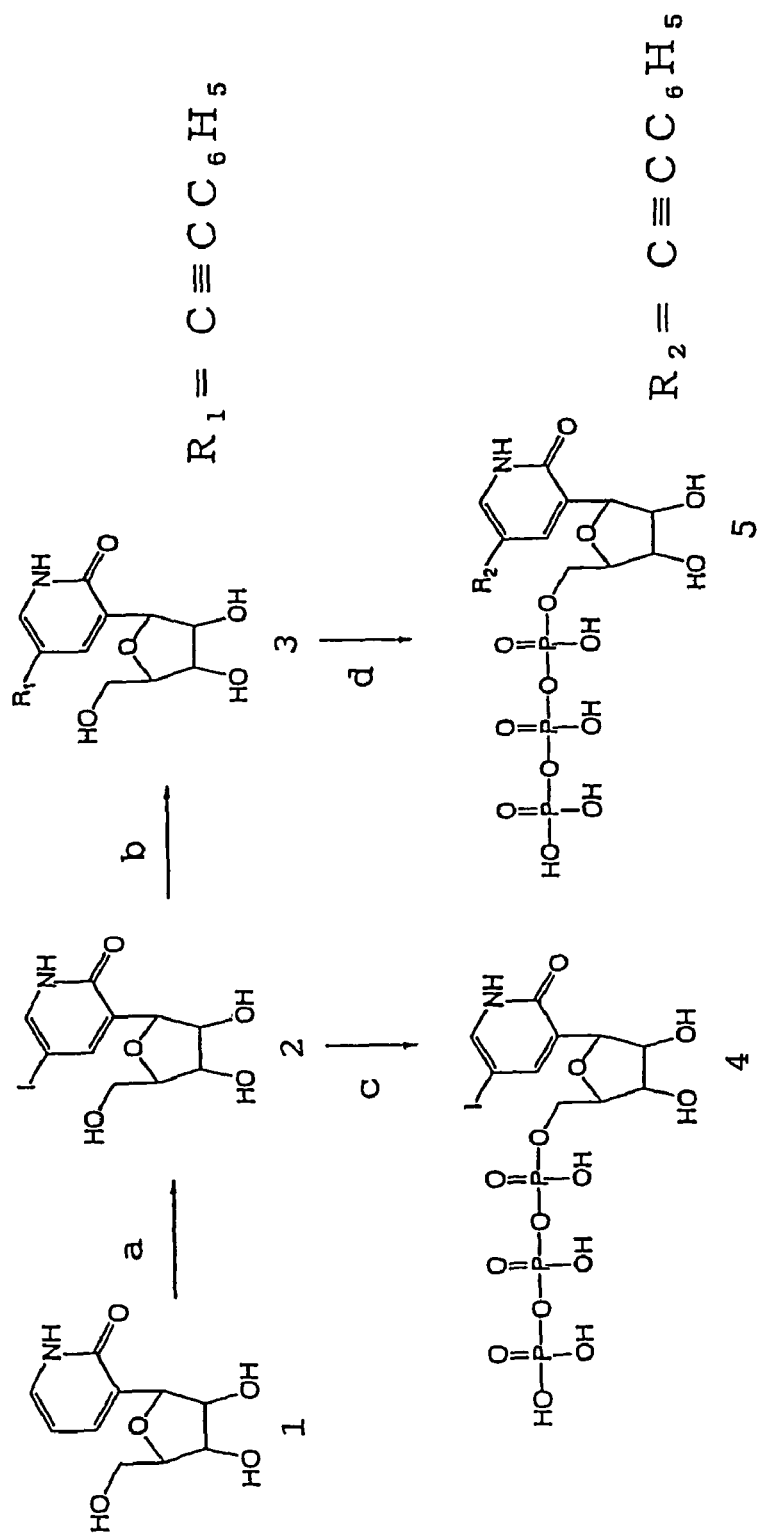
FIG. 3 shows a synthesis scheme for the compounds according to the present invention, 3-(β-D-ribofuranosyl)-5-iodopyridin-2(1H)-one 5'-triphosphate and 3-(βD-ribofuranosyl)-5-(2-phenylethynyl)-pyridin-2(1H)-one 5'-triphosphate.

Synthesis of 3-(β-D-ribofuranosyl)-5-iodopyridin-2 (1H)-one 5'-triphosphate (1) Synthesis of 3-(β-D-ribofuranosyl)-5-iodopyridin-2(1H)-one (FIG. 3, 1→2)

3-(β-D-Ribofuranosyl)-pyridin-2(1H)-one (342 mg, 1.5 mmol) (Matulic-Adamic, J., Beigelman, L., Tetrahedron Lett., 1997, 38, p. 203-206; Ishikawa, M., Hirao, I., Yokoyama, S., Tetrahedron Lett., 2000, 41, p. 3931-3934), iodine (573 mg, 2.3 mmol) and potassium iodide (KI) (657 mg, 7.9 mmol) were added to 50 mM sodium carbonate (36 ml) and heated at 110° C. for 12 hours. After the reaction, dichloromethane was added to separate the aqueous layer, followed by washing with dichloromethane. The aqueous layer was concentrated under reduced pressure and then purified by C18 reversed-phase HPLC to give 3-(β-D-ribofuranosyl)-5-iodopyridin-2(1H)-one (155 mg).

(2) Synthesis of 3-(β-D-ribofuranosyl)-5-iodopyridin-2(1H)-one 5'-triphosphate (FIG. 3, 2→4)

3-(β-D-Ribofuranosyl)-5-iodopyridin-2(1H)-one prepared in (1) above (0.1 mmol) and proton sponge (48 mg, 0.23 mmol) were dissolved in trimethyl phosphate (500 μl) and cooled to 0° C. Phosphorus oxychloride ($POCl_3$) (13 μl, 1.3 equivalents) was added to this solution and stirred at 0° C. for 4 to 5 hours, followed by sequential addition of tri-n-butylamine (119 μl, 5.0 equivalents) and a 0.5 μM bis(tributylammonium) pyrophosphate solution (in dimethylformamide) (1.0 ml, 5.0 equivalents) (Ludwig. J., Eckstein, F., J. Org.

Chem., 1989, 54, p. 631-635). After 30 minutes, 0.5 M triethylammonium bicarbonate (500 µl) was stirred. The reaction mixture was purified sequentially by DEAE sephadex A-25 and C18 reversed-phase HPLC to give the titled compound 3-(β-D-ribofuranosyl)-5-iodopyridin-2(1H)-one 5'-triphosphate (herein also referred to as "5IyTP").
ESI-Mass
Calculated: 593.05, Found: 591.70(M–H)

Example 2

Synthesis of 3-(β-D-ribofuranosyl)-5-(2-phenylethynyl)-pyridin-2(1H)-one 5'-triphosphate (1) Synthesis of 3-(β-D-ribofuranosyl)-5-(2-phenylethynyl)-pyridin-2(1H)-one (FIG. 3, 2→3)

3-(β-D-Ribofuranosyl)-5-iodopyridin-2(1H)-one prepared in Example 1(1) (71 mg, 0.20 mmol) was dissolved in DMF (1.0 ml), followed by addition of CuI (6 mg, 0.032 mmol), triethylamine (42 µl, 0.30 mmol), phenylacetylene (33 µl, 0.30 mmol) and Pd(Ph$_3$P)$_4$ (11 mg, 0.010 mol). The reaction mixture was stirred under an argon atmosphere at room temperature for 6 hours. After addition of ethyl acetate (10 ml), the reaction mixture was extracted three times with water (10 ml each). The combined aqueous layers were concentrated under reduced pressure and then purified by reversed-phase HPLC to give 3-(β-D-ribofuranosyl)-5-(2-phenylethynyl)-pyridin-2(1H)-one (60 mg, 92%) as a white product.
$^1$H-NMR (270.16 MHz, methanol-d$_4$); δ 7.86 (dd, 1H, J=0.8, 2.4 Hz, 6), 7.62 (dd, 1H, J=0.3, 2.4 Hz, 4), 7.46 (m, 2H, phenyl), 7.35 (m, 3H, phenyl), 4.85 (d, 1H, J=4.9 Hz, 1'), 4.12 (t, 1H, J=4.9 Hz, 3'), 4.00-4.07 (m, 2H, 2', 4'), 3.84 (dd, 1H, J=2.7, 12.2 Hz, 5'), 3.70 (dd, 1H, J=3.8, 12.2 Hz, 5'). ESI-MS (negative); 325.85[M–H]. λmax=287 nm (ε=7.7×10$^3$)

(2) Synthesis of 3-(β-D-ribofuranosyl)-5-(2-phenylethynyl)-pyridin-2(1H)-one 5'-triphosphate (FIG. 3, 3→5)

5-(2-Phenylethynyl)-3-(β-D-ribofuranosyl)-pyridin-2 (1H)-one prepared in (1) above (14 mg, 0.043 mmol) and 1,8-bis(dimethylamino)naphthalene (14 mg, 0.068 mmol) were dissolved in trimethyl phosphate (0.43 ml). Under ice cooling, phosphorus oxychloride (5.2 µl, 0.056 mmol) was added to this solution and stirred at 0° C. for 2 hours. A mixture of tributylamine (52 µl) and a 0.5 M bistributylammonium pyrophosphate solution (in dimethylformamide) (0.43 ml) was added and stirred at 0° C. for 10 minutes. After addition of TEAB (5 ml, 50 mmol), the reaction mixture was purified at 4° C. on a DEAE sephadex anion exchange column with 0.05-1M gradient TEAB. A fraction containing the titled compound 3-(β-D-ribofuranosyl)-5-(2-phenylethynyl)-pyridin-2(1H)-one 5'-triphosphate was lyophilized to give the compound of interest (27 mg, 65%). The final product was further purified by reversed-phase HPLC.
ESI-MS (negative); 565.58[M–H]

Example 3

Determination of the Concentration and Molar Absorption Coefficient of Unnatural Base-containing Nucleoside Triphosphates To determine the concentration of each unnatural base-containing nucleotide (dNTP/NTP) (e.g., the inventive nucleoside or nucleotide having a 5-substituted-2-oxo(1H)-pyridin-3-yl group as a base), each nucleotide was treated with alkaline phosphatase to cleave phosphoester bonds and then measured for the content of inorganic phosphate. To determine the molar absorptivity, epsilon (ε), of each nucleoside triphosphate, the absorbance at a peak wavelength and the absorbance Abs at a wavelength of 260 nm were measured in 10 mM phosphate buffer (pH 7) and used to calculate ε according to the equation: ε=Abs/Conc (Conc: dNTP/NTP concentration).

FIG. 4 shows the UV absorption of 5IyTP prepared in Example 1. 5IyTP has an absorption peak at a wavelength around 318 nm.

Alkaline phosphatase cleavage of phosphoester bonds was accomplished by incubating at 42° C. for 1 hour a reaction solution (40 µl scale) containing a test nucleoside 5'-triphosphate, 50 mM Tris-HCl (pH 9.0), 1 mM MgCl$_2$ and 20 units of Calf intestine-derived alkaline phosphatase (TaKaRa). Phosphorus quantification was performed according to the method of Chen [Chen et al., 1956]. One-half volume (20 µl) of the reaction solution was added to 4 ml water and 4 ml Reagent C (a solution prepared by mixing 6N sulfuric acid, distilled water, 2.5% ammonium molybdate solution and 10% L-(+) ascorbic acid at 1:2:1:1 by volume) and then reacted by shaking at 37° C. for 2 hours. The reacted sample was restored to room temperature and measured for its absorbance at 820 nm to calculate the phosphorus content from a calibration curve.

Example 4

Preparation of Template DNAs for Site-Selective Introduction of 5IyTP Into RNA9A s:y base pairing between the above-mentioned 2-amino-6-thienylpurine (s) and pyridin-2-one (y) having a hydrogen atom at a position complementary to the bulky substituent of s is not selective enough to resist PCR-based DNA amplification. However, template DNAs can be amplified by PCR using an s-containing primer. Within the 3'-terminal region of RNA 9A (100 nucleotides in total length) prepared in Reference Example 1, which region had been found to be not important for interaction with Raf-1 RBD, C84, C87 and A92, each being flanked by two purine bases, were selected as sites for 5Iy introduction.

More specifically, the vector TOPO-9A (containing the subcloned aptamer RNA 9A) prepared in Reference Example 1 was first cleaved at one BamHI site to prepare linearized double-stranded DNA (dsDNA) for use as a PCR template. RNA9A has a sequence composed of 100 bases shown in SEQ ID NO: 1 and FIG. 5b). In FIG. 5b), the underlined bases 84, 87 and 92 are sites used for 5Iy introduction. As PCR primers, the following were used: a sense primer consisting of the nucleotide sequence shown in SEQ ID NO: 2 and an antisense primer consisting of the nucleotide sequence shown in any one of SEQ ID NOs: 3-7.

```
Sense primer:
ggtaatacga ctcactatag ggagtggagg aattcatcg    39
(SEQ ID NO: 2)

Antisense primer:
gcagaagctt gctgtcgcta aggcatatg    29
(SEQ ID NO: 3)

gcagaagctt gctgtcsgcta aggcatatg    29
(SEQ ID NO: 4)
```

-continued

```
gcagaagctt gctgtcgcta aggcatatg          29
(SEQ ID NO: 5)

gcagaagcst gctgtcgcta aggcatatg          29
(SEQ ID NO: 6)

gcagaagcst gctgtcscta aggcatatg          29
(SEQ ID NO: 7)
```

Nucleotides 19-39 of the sense primer (SEQ ID NO: 2) correspond to nucleotides 1-20 of RNA9A (SEQ ID NO: 1). Nucleotides 3-18 of SEQ ID NO: 2 include a sequence complementary to T7 promoter.

For use as a 3'-terminal antisense primer, the following primers were chemically synthesized: 29.45 having a sequence complementary to the constant region (72-100) of RNA 9A (SEQ ID NO: 1), 29.45s84, 29.45s87 and 29.45s92 containing s at a single site, and 29.45s84/92 containing s at two sites (FIG. 5b). These primers were used in PCR to amplify s-containing template DNAs, as shown below.

A phosphoamidite of 2-amino-6-thienylpurine (s) used in a primer can be synthesized in a known manner, e.g., as described in Fujiwara et al., 2001.

To avoid removal of s during PCR, the PCR reaction was accomplished by using Taq DNA polymerase (TaKaRa Taq™) lacking 3'→5' exonuclease activity. The reaction composition is as follows: 10 mM Tris-HCl (pH 8.3), 50 mM KCl, 1.5 mM MgCl$_2$, 0.2 mM dNTPs, 1 μm each primer, 1 ng/μl template dsDNA, and 0.025 U/μl Taq DNA polymerase. The reaction was performed using a PTC-100™ Program Themal Controller under the following conditions: [94° C. for 30 seconds, 40° C. for 30 seconds, 60° C. for 1 minute]×15 or 20 cycles, 60° C. for 5 minutes.

After the reaction solutions were extracted with phenol/chloroform, the supernatants were precipitated with ethanol to collect PCR products. In the case of using 29.45s84 and 29.45s84/92 primers in which s was located relatively near the 3'-terminus, the efficiency of PCR amplification was slightly reduced, but PCR products of sufficient purity for transcription reaction could be obtained (not shown). Each PCR product was dissolved in 10 mM Tris-HCl (pH 7.6) containing 10 mM NaCl and stored for use as a template for the subsequent T7 transcription reaction.

Example 5

Transcription Reaction with T7 RNA Polymerase

In this example, the PCR products obtained in Example 4 were each used as a template in transcription reaction with T7 RNA polymerase to create various RNA 9A variants having 5Iy prepared in Example 1 at a specific 3'-terminal site(s).

The reaction composition of T7 transcription may be the same as described in Ohtsuki et al., 2001. Details are as follows: 40 mM Tris-HCl (pH 8.0), 5 mM DTT, 24 mM MgCl$_2$, 2 mM spermidine, 0.01% TritonX-100, 10 mM GMP, 1 mM NTPs, 0-0.25 mM 5IyTP, 0.2 μl/μl template DNA, and 2.5 U/μl T7 RNA polymerase (TaKaRa). After enzymatic reaction at 37° C. for 6 hours, each reaction product was purified by electrophoresis on an 8% polyacrylamide-7M urea gel.

FIG. 6a) shows an electrophoresis autoradiogram of transcription products obtained in the presence (+) or absence (−) of 0.25 mM 5Iy. FIG. 6b) shows the secondary structure of RNA9A, in which the positions where 5Iy is introduced are marked with solid circles. As shown in FIG. 6, the transcription reaction proceeded efficiently in the presence of 0.25 mM 5Iy ribonucleoside triphosphate (5IyTP) and a product of 100 nucleotides in total length could be confirmed by gel electrophoresis.

Even when 3-(β-D-ribofuranosyl)-5-(2-phenylethynyl)-pyridin -2(1H)-one 5'-triphosphate prepared in Example 2 was used instead of 5IyTP, the transcription reaction was also confirmed to proceed.

Example 7

Base Composition Analysis of Transcription Products

To examine the level of selective incorporation of 5Iy into the full-length reaction products obtained in Example 5, base composition analysis was performed on RNAs. When T7 transcription reaction is performed in the presence of [α-$^{32}$P] ATP or [α-$^{32}$P]GTP, a nucleoside 3'-phosphate (Np) 5'-terminal to A or G is labeled with $^{32}$P. Each gel-purified RNA was completely digested into Np by RNase T$_2$ (Sigma). If 5Iy is introduced at residue 84 or 92, the nucleoside 3'-phosphate of 5Iy (5IyTp) is labeled with $^{32}$P via [α-$^{32}$P]GTP, while if 5Iy is introduced at residue 87, 5IyTp is labeled via [α-$^{32}$P]ATP (FIG. 5, FIG. 6-b). For base composition analysis of 5Iy-containing RNAs, each of the completely digested products was separated by 2D-TLC and determined for each nucleotide content.

More specifically, to completely digest RNA, 0.75 μl RNase T$_2$ solution (5 units/μl; 100 mM NaOAc pH 4.5, 10% glycerol) was added to 4.25 μl aqueous solution containing the labeled RNA and a 0.25 OD E. coli-derived tRNA mixture (Sigma), followed by overnight enzymatic reaction at 37° C. A part of the reaction solution was spotted onto a 10 cm×10 cm TLC plate (Funacell SF; Funakoshi Co., Ltd., Japan) and developed in two dimensions. Developing solutions for the first and second dimensions are isobutyric acid/ammonia/water (66:1:33 by volume) and 2-propanol/hydrochloric acid/water (70:15:15 by volume), respectively. The developed spots were detected and quantified using a bioimaging analyzer (BAS2500, Fuji Photo Film Co., Ltd., Japan).

FIG. 7 and Table 1 show the results obtained.

TABLE 1

| | Base composition analysis of transcription products | | | | | | | |
|---|---|---|---|---|---|---|---|---|
| RNA | $^{32}$P label | 5IyTP | Ap | Gp | Cp | Up | 5Iyp | misincorporation* |
| 9A | ATP | − | 5.91(6) | 5.97(6) | 7.02(7) | 6.11(6) | | |
| | ATP | + | 5.92(6) | 6.01(6) | 6.95(7) | 6.10(6) | 0.10(0) | 0.45% |
| | GTP | − | 7.84(8) | 4.91(5) | 4.19(4) | 5.06(5) | | |
| | GTP | + | 7.77(8) | 5.03(5) | 4.18(4) | 4.93(5) | 0.09(0) | 0.41% |

TABLE 1-continued

Base composition analysis of transcription products

| RNA | $^{32}$P label | 5IyTP | Ap | Gp | Cp | Up | 5Iyp | misincorporation* |
|---|---|---|---|---|---|---|---|---|
| 9A(5IyB4) | ATP | + | 5.91(6) | 5.99(6) | 7.02(7) | 5.97(6) | 0.12(0) | 0.41% |
|  | GTP | + | 7.81(8) | 5.00(5) | 3.10(3) | 5.13(5) | 0.97(1) |  |
| 9A(5Iy87) | ATP | + | 5.86(6) | 5.98(6) | 6.11(6) | 6.03(6) | 1.04(1) |  |
|  | GTP | + | 7.93(8) | 5.03(5) | 4.04(4) | 4.94(5) | 0.06(0) | 0.27% |
| A(5Iy92) | ATP | + | 4.89(5) | 5.94(6) | 7.09(7) | 5.97(6) | 0.11(0) | 0.46% |
|  | GTP | + | 6.90(7) | 5.02(5) | 4.23(4) | 4.86(5) | 0.98(1) |  |
| 9A(5Iy84/92) | ATP | + | 5.09(5) | 5.74(6) | 7.07(7) | 5.98(6) | 0.12(0) | 0.5% |
|  | GTP | + | 6.94(7) | 4.98(5) | 3.16(3) | 4.92(5) | 2.00(2) |  |

Each value was calculated from the following equation. The theoretical numbers of nucleotides are in parentheses.

$$\frac{[^{32}P \text{ counts in each nucleotide(Np)}]}{[^{32}P \text{ counts in all nucleotides}]} \times [\text{total number of } 5'\text{-terminal} A \text{ or } G^{**} \text{ nucleotides}]$$

*[value for 5Iyp]/[total number of 5'-terminal A or $G^{**}$ nucleotides] × 100(%)

**pGp counts were excluded for G

The results indicated that 5Iy was incorporated opposite s in the template with high selectivity (97% or more) and the misincorporated 5Iy constituted only less than 0.5% of the total. This indicated that 5Iy could be site-selectively introduced into RNA when an s-containing primer was used in PCR to prepare a template from a sequence within a plasmid.

Example 8

Binding Efficiency of Each 5Iy-Containing RNA to Raf-1 RBD

In this example, to examine changes in binding activity to Raf-1 RBD, each RNA site-selectively introduced with 5Iy was measured for binding efficiency by a filter binding method (Table 2). 9A(5Iy84), 9A(5Iy87) and 9A(5Iy92), each being introduced with 5Iy at a single site, showed a binding efficiency equal to that of 5Iy-free RNA 9A. In contrast, 9A(5Iy84/92) introduced with 5Iy at two sites showed a reduced binding efficiency. Likewise, RNA 9A(5IU) which was randomly introduced with 5-iodo U (5IU) on an average of 5-6 bases per molecule also showed a reduced binding capacity. These results indicated that at least when a single 5Iy was introduced into RNA 9A at residue 84, 87 or 92, the introduced 5Iy did not substantially affect the binding activity of aptamers. This means that the inventive method for site-selective introduction of 5Iy is advantageous.

TABLE 2

Binding efficiency of each 5Iy-containing RNA to Raf-1 RBD

| RNA | Raf-1 RBD binding % | Filter binding % |
|---|---|---|
| 9A | 25 (5) | 0.2 (0.1) |
| 9A(5IU)$^a$ | 16 (3) | 0.3 (0.2) |
| 9A(5Iy)$^b$ | 24 (2) | 0.08 (0.03) |
| 9A(5Iy84) | 21 (5) | 0.1 (0.1) |
| 9A(5Iy87) | 22 (2) | 0.06 (0.04) |
| 9A(5Iy92) | 25 (2) | 0.1 (0.1) |
| 9A(5Iy84/92) | 15 (2) | 0.2 (0.1) |

The binding efficiency to Raf-1 RBD was measured for each RNA by a filter binding method (Raf-1 RBD/RNA=300:5 nM). The experiment was performed in triplicate and the values averaged for each sample were shown in the table. Standard deviations are in parentheses. $^a$ RNA 9A transcribed from s-free template DNA in the presence of 0.4 mM 5IUTP. $^b$ RNA 9A transcribed from s-free template DNA in the presence of 0.25 mM 5IyTP.

Example 9

Crosslinking Reaction by UV Irradiation

In this Example, each RNA site-selectively containing 5Iy was measured for light irradiation-induced crosslinkability.

Each RNA whose 5'-terminus was $^{32}$P-labeled was warmed in Buffer A at 75° C. for 3 minutes and then allowed to stand at room temperature for 10 minutes or longer to form the secondary structure of RNA. On the other hand, to prepare Raf-1 RBD, human Raf-1 RBD (amino acid residues 51-131) was expressed as a GST (glutathione transferase)-fusion protein in E. coli cells and purified from the supernatant of crushed cells by column chromatography. Rat RGL RBD (amino acid residues 632-734) [Koyama et al., 1996] and human B-Raf RBD (amino acid residues 149-226) were also expressed as GST-fusion proteins in E. coli cells and purified in the same manner.

A solution of each RNA folded into a secondary structure was supplemented with an equal volume of a Raf-1 GST-RBD solution (containing, in addition to RBD, 160 µg/ml BSA, 1 mM DTT and 7.3% glycerol in Buffer A) and incubated at 37° C. for 30 minutes to form RNA-RBD complexes. The resulting samples were dispensed in 40-120 µl aliquots into wells of a 96-well multiwell plate (COASTAR) on ice. The plate was covered with a polystyrene lid to reduce UV of 300 nm or shorter wavelength, and then irradiated using a UV transilluminator (TVC-312R/J Spectronics, UV wavelength: 312 nm) from a distance about 1 cm for 1 hour.

The wavelength of UV used as a light source was selected by taking into account that the absorption peak wavelength of 5IyTP was around 318 nm (FIG. 4). On the other hand, in the case of using a UV transilluminator, the irradiation wavelength would be broadened between 270 and 400 nm (as shown in the spectrum chart of 8/15 W medium wave UV-B fluorescent tubes (not shown)) [Meisenheimer & Koch, 1997]. For this reason, in this example, UV irradiation was performed with the samples covered with a polystyrene lid in order to reduce as much as possible the amount of 300 nm or shorter wavelength light which overlapped with the absorption wavelength of natural bases.

The reaction solutions were electrophoresed on 8% polyacrylamide-7M urea gels, followed by product analysis. To collect crosslinked products, the reaction solutions were extracted with phenol/chloroform and electrophoresed to separate the crosslinking products, which were then extracted from the gel. As a result, in RNAs, 9A(5Iy84) and 9A(5Iy87) containing 5Iy at residue 84 or 87, bands of crosslinking reaction products were clearly detected at different positions from unreacted RNA (100 nucleotides) (FIG. 8, Lanes 6 and 8).

A further attempt was made to identify the crosslinking reaction products. Since RNA 9A is an aptamer binding to Raf-1 RBD, crosslinking reaction between RNA and GST-RBD can be believed as a possible candidate of the reaction mechanism. When UV irradiation was performed in the absence of GST-RBD, bands of crosslinking reaction products were detected although they were slight (FIG. 9, Lanes 1 and 5). In further experiments, these RNAs were irradiated with UV in the presence of GST-RBD and then treated with proteinase K (PK) or extracted with phenol/chloroform (phenol) to remove the protein, indicating that there was no change in the bands (FIG. 9, Lanes 2-4 and 6-8).

These results indicated that the crosslinking reaction products did not result from crosslinking between RNA and protein (GST-RBD). In view of the findings that even the RNAs alone produced detectable crosslinking reaction products and that the band mobility of crosslinking products was substantially comparable to that of RNA 9A dimers (not shown), it would be RNA molecules dimerized in the presence of GST-RBD that were obtained by crosslinking reaction. It was also indicated that such aptamer dimerization was accelerated in the presence of proteins.

Example 10

Dimerization of RNA 9A by Crosslinking Reaction

GST protein is more likely to dimerize and actually used as a domain for protein dimerization [Inouye et al., 2000]. Thus, GST-RBD used in this example would dimerize in solution and RNA 9A molecules, when binding to the RBD moiety, would approach each other to cause crosslinking between RNA molecules. In this case, crosslinking reaction products still have the possibility of retaining the binding activity to Raf-1 RBD.

The product (XL) obtained by crosslinking reaction an equal concentration (0.1 µM) mixture of 9A(5Iy87) and Raf-1 RBD was purified from a gel and analyzed for binding between XL and GSTRBD by gel shift assay. As a control of RNA 9A dimer, RNA 9A molecules were also linked in tandem to newly prepare RNA 9A×2 (200 nucleotides in total length), followed by gel shift assay. RNA 9A×2 is an RNA molecule of 200 nucleotides in total length that has two essential regions of RNA 9A (residues 1-80) in its molecule. It was prepared by transcription reaction using T7 RNA polymerase (Epicentre) and subcloned into vector pCR®II-TOPO (Invitrogen).

Gel Shift Assay

Each RNA whose 5'-terminus was $^{32}$P-labeled (0.8 pmol) was warmed in 20 µl Buffer A at 75° C. for 3 minutes and then allowed to stand at room temperature for 10 minutes or longer to form the secondary structure of RNA. This RNA solution was supplemented with a solution of *E. coli* derived tRNA mixture (100 µg/ml; a sample purchased from Sigma, gel-purified before use) in 20 µl Buffer A, allowed to stand at room temperature for 5 minutes or longer, and then divided into 5 µl aliquots. Each aliquot was supplemented with 5 µl Raf-1 GST-RBD solution (containing, in addition to RBD, 160 µg/ml BSA, 1 mM DTT and 10% glycerol in Buffer A), incubated at 37° C. for 30 minutes, and then analyzed by electrophoresis on a 5% non-denaturing polyacrylamide gel (acrylamide:bisacrylamide=39:1).

Electrophoresis was performed at room temperature and at a constant voltage (150 V) for about 2 hours (gel size: 16 cm×16 cm×1 mm). The composition of electrophoresis buffer is as follows: 12.5 mM Tris and 125 mM Glycine. Each electrophoresed gel was dried using a gel dryer and analyzed with a bioimaging analyzer (BAS2500, Fuji Photo Film Co., Ltd., Japan).

As expected, the band pattern of gel shift indicated that 1 molecule of RNA XL showed efficient complex with 2 molecules of GST-RBD (FIG. 10*c*). In view of the finding that the band mobility of RNA XL in the absence of GST-RBD was substantially the same as that of RNA 9A×2, XL was also confirmed to be a dimerization product of RNA 9A (FIGS. 10*c* and *d*). The gel shift pattern also suggested that the binding activity to 2 molecules of GST-RBD was higher in RNA XL than in RNA 2×9A. This is because the orientation of Raf-1 RBD molecules dimerized via the GST tag may be successfully matched with the RBD-binding moiety of RNA XL. In contrast, RNA 9A formed a 1:1 complex with GST-RBD (FIG. 10*a*). In RNA OC showing negligible binding to Raf-1 RBD, no gel shift was observed even when the GST-RBD concentration was increased (FIG. 10*b*).

These results indicated that the site-selective introduction of 5Iy into RNA 9A enabled the provision of GST-RBD-dependent crosslinkability between RNA molecules. It was also shown that 5Iy could be adapted for analysis of intermolecular interactions and that an artificial base pair s:5Iy was useful in designing nucleic acids having new functions.

Reference Example 1

Isolation of RNA Aptamers Specifically Binding to Raf-1 Protein

In this reference example, RNA aptamers specifically binding to Raf-1 protein were isolated by in vitro selection techniques. Such RNA molecules were found to act as cellular signaling molecules regulating protein-protein interactions.

Raf-1 protein is a 74 kDa serine/threonine protein kinase expressed in the cytoplasm and is a gene product of c-raf-1 found as a cancer gene [Rapp et al., 1988]. In mammalian cells, A-Raf and B-Raf are known as isoforms of Raf-1. Raf-1 is activated by interaction with a membrane-bound protein Ras, and it is being shown that other proteins as well as Ras also contribute to the regulatory mechanism [Kolch, 2000]. The Ras protein is a gene product of ras found as a cancer gene and is a low-molecular-weight G protein which binds to GDP or GTP [Campbell et al., 1998]. As in the case of other G proteins, Ras is converted into an activated form when bound to GTP. This GTP-bound Ras has been identified to bind to a domain of Raf-1 consisting of amino acid residues 51 to 131

(Ras-binding domain; RBD). Raf-1 activation is believed to require some conformational change on the membrane triggered by Ras/Raf interaction, as well as additional interactions with other factors.

In this reference example, In vitro selection techniques were used to try to design a regulatory molecule which selectively inhibited only Ras/Raf interaction. In relation to proteins whose interaction with nucleic acids has been unknown, it is also possible to artificially obtain DNA and/or RNA molecules (aptamers) specifically binding to the proteins when using in vitro selection techniques. Such in vitro selection is an approach in which a series of processes (round) for selection and amplification is repeated to select molecular species having specific functions from a nucleic acid library (pool) containing random sequences (FIG. 11) [Ellington & Szostak, 1990].

In this reference example, with the aim of designing a novel RNA molecule selectively regulating Ras/Raf-1 interaction in cellular signal transduction, RNA aptamers specifically binding to Raf-1 RBD were isolated by in vitro selection techniques. An RNA aptamer obtained from a pool containing random sequences of 60 nucleotides ($N_{60}$) inhibited Raf-1 RBD/Ras interaction. However, this RNA aptamer had a weak inhibitory capacity, and a large excess of RNA was required for Ras inhibition. In response to this, the selection technique was partially modified and used for selection on a pool containing newly designed RNA random sequences of 45 nucleotides ($N_{45}$). The RT-PCR products were each subcloned into TA cloning vector pCR®II-TOPO using a TOPO TA Cloning Kit Dual (Invitrogen), and nucleotide sequences were determined for individual clones using a dRhodamine Terminator Cycle Sequencing Ready Reaction Kit (Applied Biosystems). As a result, two RNA aptamers (RNA 9A, RNA 9B) having a higher inhibitory capacity were obtained.

RNA 9A, which was found to have a particularly high inhibitory capacity, strongly inhibited Ras-induced Raf-1 activation in a cell-free system based on the membrane fraction of Sf9 cells expressing Ras and Raf-1 as well as on the cytoplasmic fraction of HEK293 cells, indicating that RNA 9A acted as an artificial regulatory molecule. Moreover, although RNA 9A would bind to the RBD of B-Raf, an isoform of Raf-1 (FIG. 12), it did not inhibit B-Raf RBD/Ras interaction. This indicated that RNA 9A showed specific inhibition against Ras/Raf-1 interaction. Further, RNA 9A was estimated to form a pseudoknot structure, as indicated by the results of RNA secondary structure analysis using limited hydrolysis with RNase and chemical modification, as well as by the experimental results obtained in truncated RNA variants (FIG. 13). Also, region of RNA 9A interacting with the Raf-1 RBD was examined by footprinting using chemical modification, suggesting that a specific loop segment(s) was located on the Raf-1 RBD-binding surface.

Example 11

Synthesis of y Derivative Labeled with Biotin Via Ethylenic Linker (FIG. 15)

Synthesis of N-Allylbiotinamide (Compound 2 in FIG. 15)

In an argon-purged 100 ml flask, biotin-N-hydroxy-succinimide (251 mg, 0.735 mmol; Compound 1, Sigma-Aldrich) was dissolved in 26.7 ml dry DMF and mixed with allylamine (50 μl, 0.668 mmol; Nacalai Tesque, Inc., Japan), followed by stirring at room temperature with the flask covered with aluminum foil for light shielding. The progress of the reaction was monitored by C18 reversed-phase HPLC (HPLC conditions; column: μ-Bondsphere φ19×150 mm (Waters); mobile phase: 20% acetonitrile in $H_2O$; elution speed: 10 ml/min; detection: UV absorption (200 nm)). At 3 hours after initiation of the reaction, it was confirmed that the source material biotin-N-hydroxysuccinimide was almost completely converted into Compound 2. This reaction solution was used directly in the subsequent reaction.

Synthesis of biotinylated 5-(3-amino-1-propenyl)-3-(β-D-ribofuranosyl)-2-pyridone (Compound 4 in FIG. 15) and biotinylated 5-(3-amino-1-propen-2-yl)-3-(β-D-ribofuranosyl)-2-pyridone (Compound 5 in FIG. 15)

The reaction solution of Compound 2 (in which 0.668 mmol of Compound 2 was dissolved in 26.7 ml dry DMF) was mixed with a solution of 5-iodo-3-(β-D-ribofuranosyl)-2-pyridone (118 mg, 0.334 mmol; I-ry, Compound 3) and disodium tetrachloropalladate (98.3 mg, 0.334 mmol; Sigma-Aldrich) in a 0.1M sodium acetate solution (26.7 ml, pH 5.2), followed by stirring under an argon atmosphere at room temperature for 20 hours. After completion of the reaction, the solvent was distilled off and the residue was suspended in $H_2O$. The resulting suspension was passed through a reversed-phase column (stationary phase: Cosmosil 140 C18-prep (Nacalai Tesque, Inc., Japan); mobile phase: 40% acetonitrile in $H_2O$) to collect a fraction containing the product (detected by UV absorption (260 nm)), followed by evaporation. The resulting residue was dissolved in $H_2O$ and the product was purified by C18 reversed-phase HPLC (HPLC conditions; column: μ-Bondsphere φ19×150 mm (Waters); mobile phase: Solvent A=$H_2O$, Solvent B=50% acetonitrile in $H_2O$, 0-15 minutes, 10-80% B, 15-15.5 minutes, 80-100% B, 15.5-18 minutes, 100% B, 18-19 minutes, 100-10% B, 19-24 minutes, 10% B; elution speed: 10 ml/min; detection: UV absorption (260 nm and 318 nm)). The yield of the HPLC-purified product was 47.4 mg (0.093 mmol, 27.9% from Compound 3).

The purified product was found to be a mixture of Compounds 4 and 5. To separate Compounds 4 and 5, HPLC purification was repeated under different conditions (HPLC conditions; column: μ-Bondsphere φ19×150 mm (Waters); mobile phase: 9% acetonitrile in $H_2O$; elution speed: 10 ml/min; detection: UV absorption (260 nm and 318 nm)). The ratio of Compounds 4 and 5 obtained was 4:5=0.53:0.47, as determined from the ratio of integrated ethylene proton values measured for individual compounds by $^1$H-NMR (—CH=CH—for Compound 4, >C=$CH_2$ for Compound 5).

Structural analysis data for Compound 4; $^1$H-NMR (DMSO-$d_6$), δ (ppm) 1.19-1.68 (6H, m, —C$\underline{H}_2$C$\underline{H}_2$C$\underline{H}_2$$CH_2$—C(O)NH—), 2.10 (2H, t, —C$\underline{H}_2$—C(O)NH—, J=7.3 Hz), 2.57 (1H, d, —CHC$\underline{H}_2$S—, J=12.7 Hz), 2.81 (1H, dd, —CHC$\underline{H}_2$S—, J=4.7, 12.4 Hz), 3.06-3.12 (1H, m, —CHC$\underline{H}$S—), 3.34-3.66 (2H, m, H5', 5"), 3.76-3.93 (5H, m, H2', 3', 4', —C(O)NHC$\underline{H}_2$—), 4.09-4.14 (1H, m, —NHC$\underline{H}$CHS—), 4.27-4.32 (1H, m, —NHC$\underline{H}$C$H_2$S—), 4.66-4.71 (2H, m, H1', 3'-OH), 5.04-5.13 (2H, m, 2'-OH, 5'-OH), 5.93 (1H, dt, —$CH_2$C$\underline{H}$=CH—, J=5.5, 16.0 Hz), 6.25 (1H, d, —$CH_2$CH=C$\underline{H}$—, J=15.8 Hz), 6.36 (1H, s, —N$\underline{H}$CHC$H_2$S—), 6.42 (1H, s, —N$\underline{H}$CHCHS—), 7.32 (1H, s, H6), 7.90 (1H, s, H4), 7.96 (1H, t, —C(O)N$\underline{H}$C$H_2$—, J=5.1 Hz), 11.72 (1H, bs, H1);

$^{13}$C-NMR (DMSO-$d_6$), δ (ppm) 25.3, 28.2, 35.1, 55.4, 59.2, 61.1, 70.7, 74.4, 81.0, 83.6, 115.2, 123.6, 125.7, 130.7, 131.7, 134.1, 160.9, 162.5, 171.6; Electron spray mass spectrum, [M−H]⁻ (negative)=507.30 (found), 507.19 (calcd.), [M+Na]⁺ (positive)=531.28 (found), 531.19 (calcd.); UV absorption spectrum (H$_2$O), $\lambda_{max}$=262 nm, 325 nm, $\lambda_{min}$=291 nm.

Structural analysis data for Compound 5; ¹H-NMR (DMSO-d$_6$), δ (ppm) 1.12-1.64 (6H, m, —CH$_2$CH$_2$CH$_2$CH$_2$—C(O)NH—), 2.08 (2H, t, —CH$_2$—C(O)NH—, J=7.1 Hz), 2.55 (1H, d, —CHCH$_2$S—, J=12.5 Hz), 2.81 (1H, dd, —CHCH$_2$S—, J=5.1, 12.4 Hz), 2.99-3.06 (1H, m, —CHCHS—), 3.46-3.67 (2H, m, H5', 5''), 3.79-4.10 (6H, m, H2', 3', 4', —C(O)NHCH$_2$—, —NHCHCHS—), 4.26-4.31 (1H, m, —NHCHCH$_2$S—), 4.67-4.71 (2H, m, H1', 3'-OH), 5.04-5.13 (3H, m, 2'-OH, 5'-OH, >C=CH$_2$), 5.38 (1H, s, >C=CH$_2$), 6.36 (1H, s, —NHCHCH$_2$S—), 6.41 (1H, s, —NHCHCHS—), 7.34 (1H, d, H6, J=2.3 Hz), 7.96 (1H, d, H4, J=1.8 Hz), 8.06 (1H, t, —C(O)NHCH$_2$—, J=5.6 Hz), 11.79 (1H, bs, H1); ¹³C—NMR (DMSO-d$_6$), δ (ppm) 25.4, 28.1, 35.1, 41.0, 55.4, 59.1, 61.0, 70.4, 74.4, 81.0, 83.4, 110.5, 115.5, 129.9, 130.2, 135.4, 139.9, 160.8, 162.5, 171.8; Electron spray mass spectrum, [M−H]⁻ (negative)=507.29 (found), 507.19 (calcd.), [M+Na]⁺ (positive)=531.25 (found), 531.19 (calcd.); UV absorption spectrum (H$_2$O), $\lambda_{max}$=259 nm, 314 nm, $\lambda_{min}$=286 nm.

Example 12

Triphosphorylation of y Derivative Labeled with Biotin Via Ethylenic Linker (FIG. 16)

Synthesis of Biotinylated 5-(3-amino-1-propenyl)-3-(β-D-ribofuranosyl)-2-pyridone 5'-triphosphate (Bio-yTP, Compound 6 in FIG. 16)

Compound 4 (37.3 mg, 0.073 mmol) and Proton Sponge (23.6 mg, 0.11 mmol; Sigma-Aldrich) were introduced into an argon-purged 5 ml flask and suspended in 734 μl trimethylphosphate (Nacalai Tesque, Inc., Japan), followed by stirring in ice-cold water for 15 minutes. To this suspension, 8.9 μl (0.095 mmol) of phosphorus oxychloride (Nacalai Tesque, Inc., Japan) was added and stirred at 4° C. for 29 hours. After further addition of a 0.5M bis(tri-n-butylammonium)pyrophosphate-DMF solution (733 μl, 0.367 mmol) and tri-n-butylamine (87 μl, 0.367 mmol), stirring was continued for an additional 30 minutes. Subsequently, 367 μl of 0.5M TEAB (pH 7.5) was added to stop the reaction. This solution was purified on a DEAE-Sephadex A-25 column (column: DEAE-Sephadex A-25 (Amersham Biosciences) φ15 mm×300 mm, mobile phase: 50 mM to 1M TEAB (pH 7.5) linear gradient) to give Compound 6.

Synthesis of Biotinylated 5-(3-amino-1-propen-2-yl)-3-(β-D-ribofuranosyl)-2-pyridone 5'-triphosphate (Compound 7 in FIG. 16)

Compound 5 (33.1 mg, 0.065 mmol) and Proton Sponge (20.9 mg, 0.098 mmol; Sigma-Aldrich) were introduced into an argon-purged 5 ml flask and suspended in 325 μl trimethylphosphate (Nacalai Tesque, Inc., Japan), followed by stirring in ice-cold water for 15 minutes. To this suspension, 7.9 μl (0.085 mmol) of phosphorus oxychloride (Nacalai Tesque, Inc., Japan) was added and stirred at 4° C. for 23 hours. After further addition of a 0.5M bis(tri-n-butylammonium)pyrophosphate-DMF solution (650 μl, 0.325 mmol) and tri-n-butylamine (77 μl, 0.325 mmol), stirring was continued for an additional 30 minutes. Subsequently, 325 μl of 0.5M TEAB (pH 7.5) was added to stop the reaction. This solution was purified on a DEAE-Sephadex A-25 column (column: DEAE-Sephadex A-25 (Amersham Biosciences) φ15 mm×300 mm, mobile phase: 50 mM to 1M TEAB (pH 7.5) linear gradient) to give Compound 7.

Example 13

Synthesis of y Derivative Labeled with Biotin Via Acetylenic Linker (FIG. 17)

Synthesis of N-propargyl-dichloroacetamide (Compound 9 in FIG. 17)

In an argon-purged 100 ml flask, propargylamine (1.37 ml, 20 mmol; Compound 8, Sigma-Aldrich) and NaHCO$_3$ (2.02 g, 24 mmol; Nacalai Tesque, Inc., Japan) were added to 40 ml CH$_2$Cl$_2$ and stirred on ice. To this mixture, dichloroacetylchloride (2.12 ml, 22 mmol; Nacalai Tesque, Inc., Japan) was added dropwise and stirred at room temperature for 3 hours. After this solution was washed once with 5% aqueous NaHCO$_3$ solution (40 ml) and twice with saturated aqueous NaCl solution (40 ml), the organic layer was dried over Na$_2$SO$_4$, filtered and evaporated to give Compound 9. Compound 9 was obtained in a yield of 2.60 g (15.7 mmol, 78.3%).

Structural analysis data for Compound 9; ¹H-NMR (CDCl$_3$), δ (ppm) 2.26 (1H, t, —C≡CH, J=2.6 Hz), 4.06 (2H, dd, —CH$_2$—, J=2.6, 5.3 Hz), 5.88 (1H, s, Cl$_2$CH—), 6.62 (1H, bs, —NH—).

5-(Dichloroacetyl-3-amino-1-propynyl)-3-(β-D-ribofuranosyl)-2-pyridone (synthesis of Compound 10 in FIG. 17)

5-Iodo-3-(β-D-ribofuranosyl)-2-pyridone (71 mg, 0.20 mmol; I-ry, Compound 3) was introduced into a 5 ml flask and azeotroped twice with dry acetonitrile. After the residue was dissolved in 1 ml dry DMF, CuI (6.1 mg, 0.032 mmol; Nacalai Tesque, Inc., Japan), triethylamine (42 μl, 0.30 mmol; Nacalai Tesque, Inc., Japan), Compound 9 (50 mg, 0.30 mmol) and Pd(PPh$_3$)$_4$ (12 mg, 0.010 mmol; Nacalai Tesque, Inc., Japan) were added and stirred under an argon atmosphere at room temperature for 19 hours. After completion of the reaction, the reaction mixture was extracted with EtOAc/H$_2$O and the organic layer was washed twice with 10 ml H$_2$O. The aqueous layers were evaporated and filtered through a 0.22 μm filter unit, followed by purifying the product using C18 reversed-phase HPLC (HPLC conditions; column: μ-Bondsphere φ19×150 mm (Waters); mobile phase: Solvent A=H$_2$O, Solvent B=acetonitrile, 0-10 minutes, 5-20% B, 10-18 minutes, 20% B, 18-19 minutes, 20-5% B, 19-24 minutes, 5% B; elution speed: 10 ml/min; detection: UV absorption (260 nm and 318 nm)). The yield of the HPLC-purified product (10) was 25.2 mg (0.064 mmol, 32.2%).

Structural analysis data for Compound 10; ¹H-NMR (DMSO-d$_6$), δ (ppm) 3.45-3.75 (2H, m, H5', 5''), 3.78-3.87 (3H, m, H2', 3', 4'), 4.16 (2H, d, —C(O)NHCH$_2$—, J=5.3 Hz), 4.64 (1H, d, H1', J=4.3 Hz), 4.70 (1H, d, 3' —OH, J=4.8 Hz), 4.90 (1H, t, 5'-OH, J=5.4 Hz), 5.07 (1H, bs, 2'-OH), 6.47 (1H, S, Cl$_2$CH—), 7.54-7.57 (2H, m, H4, 6), 9.09 (1H, t, —C(O)NHCH$_2$—, J=5.1 Hz), 12.02 (1H, bs, H1); Electron spray mass spectrum, [M−H]⁻ (negative)=389.16 (found), 389.03 (calcd.), [M+H]⁺ (positive)=391.20 (found), 391.05 (calcd.); UV absorption spectrum (H$_2$O), $\lambda_{max}$=259 nm, 316 nm, $\lambda_{min}$=280 nm.

Synthesis of 5-(3-amino-1-propynyl)-3-(β-D-ribo-furanosyl)-2-pyridone (Compound 11 in FIG. 17)

Compound 10 (45 mg, 0.12 mmol) was introduced into a screw-capped glass bottle and dissolved in 5 ml $H_2O$. To this solution, 28% aqueous ammonia (1 ml) was added and stirred at room temperature for 26 hours.

Synthesis of biotinylated 5-(3-amino-1-propynyl)-3-(β-D-ribofuranosyl)-2-pyridone (Compound 12 in FIG. 17)

The reaction solution of Compound 11 was transferred to a 5 ml flask and evaporated. The resulting residue was azeotroped three times with dry acetonitrile and then, after addition of biotin-N-hydroxysuccinimide (43 mg, 0.13 mmol; Sigma-Aldrich), dissolved in 1 ml dry DMF. This solution was stirred at room temperature for 2 hours and then diluted with 5 ml $H_2O$, followed by purifying the product using C18 reversed-phase HPLC (HPLC conditions; column: μ-Bondsphere φ19×150 mm (Waters); mobile phase: Solvent A=$H_2O$, Solvent B=acetonitrile, 0-15 minutes, 10-40% B, 15-15.5 minutes, 40-50% B, 15.5-18 minutes, 50% B, 18-19 minutes, 50-10% B, 19-24 minutes, 10% B; elution speed: 10 ml/min; detection: UV absorption (260 nm and 318 nm)). The yield of the HPLC-purified product (12) was 35.9 mg (0.071 mmol, 61.6% from Compound 10).

Structural analysis data for Compound 12; $^1$H-NMR (DMSO-$d_6$), δ (ppm) 1.23-1.62 (6H, m, —C$\underline{H}_2$C$\underline{H}_2$C$\underline{H}_2$CH$_2$—C(O)NH—), 2.09 (2H, t, —C$\underline{H}_2$—C(O)NH—, J=7.4 Hz), 2.56 (1H, d, —CHC$\underline{H}_2$S—, J=12.9 Hz), 2.80 (1H, dd, —CHC$\underline{H}_2$S—, J=5.1, 12.5 Hz), 3.04-3.11 (1H, m, —CHC$\underline{H}$S—), 3.47-3.62 (2H, m, H5', 5''), 3.78-3.87 (3H, m, H2', 3', 4'), 4.04 (2H, d, —C(O)NHC$\underline{H}_2$—, J=5.4 Hz), 4.09-4.12 (1H, m, —NHC$\underline{H}$CHS—), 4.26-4.31 (1H, m, —NHC$\underline{H}$CH$_2$S—), 4.63 (1H, d, H1', J=4.6 Hz), 4.71 (1H, d, 3'—OH, J=4.8 Hz), 4.92 (1H, t, 5'-OH, J =5.3 Hz), 5.11 (1H, bs, 2'-OH), 6.34 (1H, s, —N$\underline{H}$CHCH$_2$S—), 6.41 (1H, s, —N$\underline{H}$CHCHS—), 7.53 (2H, s, H4, 6), 8.27 (1H, t, —C(O)N$\underline{H}$CH$_2$—, J=5.4Hz), 11.93 (1H, bs, H1); Electron spray mass spectrum, [M−H]$^-$ (negative)=505.23 (found), 507.18 (calcd.), [M+H]$^+$ (positive)=507.26 (found), 507.19 (calcd.), [M+Na]$^+$ (positive)=529.26 (found), 529.17 (calcd.); UV absorption spectrum (H$_2$O), $\lambda_{max}$=259 nm, 318 nm, $\lambda_{min}$=280 nm.

Example 14

Triphosphorylation of y Derivative Labeled with Biotin Via Acetylenic Linker (FIG. 18)

Synthesis of Biotinylated 5-(3-amino-1-propynyl)-3-(β-D-ribofuranosyl)-2-pyridone 5'-triphosphate (Bio$^2$-yTP, Compound 13 in FIG. 18)

Compound 12 (25.6 mg, 0.05 mmol) and Proton Sponge (16.2 mg, 0.075 mmol; Sigma-Aldrich) were introduced into an argon-purged 5 ml flask and suspended in 250 μl trimethylphosphate (Nacalai Tesque, Inc., Japan), followed by stirring in ice-cold water for 15 minutes. To this suspension, 6 μl (0.065 mmol) of phosphorus oxychloride (Nacalai Tesque, Inc., Japan) was added and stirred at 4° C. for 8 hours. After further addition of a 0.5M bis(tri-n-butylammonium) pyrophosphate-DMF solution (500 μl, 0.25 mmol) and tri-n-butylamine (60 μl, 0.25 mmol), stirring was continued for an additional 30 minutes. Subsequently, 250 μl of 0.5M TEAB (pH 7.5) was added to stop the reaction. This solution was purified on a DEAE-Sephadex A-25 column (column: DEAE-Sephadex A-25 (Amersham Biosciences) φ15 mm×300 mm, mobile phase: 50 mM to 1M TEAB (pH 7.5) linear gradient) to give Compound 13.

Example 15

Determination of the Concentration and Molar Absorbance Coefficient of Bio-yTP (Compound 6) and Bio$^2$-yTP (Compound 13)

Method

To determine the concentration of Bio-yTP and Bio$^2$-yTP, they were treated with alkaline phosphatase to cleave phosphoester bonds and then measured for the content of inorganic phosphate. To determine the molar absorptivity, epsilon (ε), of each nucleoside 5'-triphosphate, the absorption peak wavelength in 10 mM phosphate buffer (pH 7) and the absorbance (Abs) at a wavelength of 260 nm were measured and used to calculate E according to the equation: ε=Abs/Conc (Conc: nucleoside 5'-triphosphate concentration).

Alkaline phosphatase cleavage of phosphoester bonds was accomplished by incubating at 42° C. for 1 hour a reaction solution (40 μl scale) containing a test nucleoside 5'-triphosphate, 50 mM Tris-HCl (pH 9.0), 1 mM MgCl$_2$ and 20 units of Calf intestine-derived alkaline phosphatase (TaKaRa). Phosphorus quantification was performed according to the method of Chen [Chen et al., 1956]. One-half volume (20 μl) of the reaction solution was added to 4 ml water and 4 ml Reagent C (a solution prepared by mixing 6N sulfuric acid, distilled water, 2.5% ammonium molybdate solution and 10% L-(+) ascorbic acid at 1:2:1:1 by volume) and then reacted by shaking at 37° C. for 2 hours. The reacted sample was restored to room temperature and measured for its absorbance at 820 nm to calculate the phosphorus content from a calibration curve.

Results

Bio-yTP had absorption peak wavelengths of 326 nm and 262 nm, at which the values of epsilon were $\epsilon 326=7.5\times10^3$ and $\epsilon 262=2.9\times10^4$, respectively. Also, the value of epsilon at 260 nm was $\epsilon 260=2.8\times10^4$. Likewise, Bio$^2$-yTP had absorption peak wavelengths of 317 nm and 258 nm, at which the values of epsilon were $\epsilon 317=5.3\times10^3$ and $\epsilon 258=1.8\times10^4$, respectively. Also, the value of epsilon at 260 nm was $\epsilon 260=1.8\times10^4$.

Example 16

Site-selective Introduction of Bio-y and Bio$^2$-y Into RNA

Method

Enzymatic site-selective introduction of Bio-y and Bio$^2$-y into RNA was accomplished by transcription reaction with T7 RNA polymerase using s-containing DNA (temp35s; 35-mer) (SEQ ID NO: 8) as a template (FIG. 19). temp35s or temp35A (a control template strand, SEQ ID NO: 9) was mixed with DNA containing a complementary sequence (T7prim28N; 28-mer) (SEQ ID NO: 10) in 10 mM Tris-HCl (pH 7.6) containing 10 mM NaCl and annealed into a double-stranded form for use in the transcription reaction.

The T7 transcription reaction was performed on 20 μl scale. The composition of T7 transcription is as follows: 40 mM Tris-HCl (pH 8.0), 5 mM DTT, 8 mM MgCl$_2$, 2 mM spermidine, 0.01% TritonX-100, 10 mM GMP, 1 mM NTPs (N=A, G, C, U, Bio-yTP, Bio$^2$-yTP), 2 μCi [α-$^{32}$P]ATP, 0.5

μM double-stranded DNA, and 2.5 U/μl T7 RNA polymerase (TaKaRa) [Ohtsuki et al., 2001]. After enzymatic reaction at 37° C. for 3 hours, each reaction solution was supplemented with an equal volume of a 10M urea-containing TPE solution and warmed at 75° C. for 3 minutes to stop the reaction. Aliquot parts of the reaction solutions were then electrophoresed on a 20% polyacrylamide-7M urea gel and the [α-$^{32}$P]ATP-labeled reaction products were analyzed with a bioimaging analyzer (BAS2500, Fuji Photo Film Co., Ltd., Japan).

Results

In the presence of 1 mM ATP, GTP and Bio-yTP, Bio-y was incorporated into RNA opposite s in the template and a 15-mer product could be confirmed by gel electrophoresis (FIG. 19, Lane 2). Likewise, also in the presence of Bio-yTP together with ATP, GTP and UTP, a 15-mer product could be confirmed in which Bio-yTP was competitively and selectively incorporated opposite s in the template (FIG. 19, Lane 4). In the presence of Bio-yTP together with ATP, GTP and CTP or with ATP, GTP, UTP and CTP, a 17-mer product could be confirmed in which Bio-yTP was competitively and selectively incorporated opposite s in the template (FIG. 19, Lanes 6, 8).

Based upon the finding that the mobility of Bio-y-containing RNA was smaller than that of Bio-y-free RNA of the same length, the electrophoretic band patterns were analyzed to distinguish whether the transcription products were incorporated with Bio-y, confirming that Bio-y was selectively incorporated into RNA opposite s in the template DNA (FIG. 19, Lanes 2-8). In addition, a band corresponding to the Bio-y-containing RNA 17-mer (FIG. 19, Lane 8) was not detected in Lane 10 of FIG. 19. This suggested that there was almost no misincorporation of Bio-y opposite s-free natural nucleotides in the template. These results indicated that T7 transcription reaction using s-containing template DNA allowed site-selective introduction of Bio-y into RNA.

Bio$^2$-yTP yielded the same results as Bio-yTP. In the presence of 1 mM ATP, GTP and Bio$^2$-yTP, Bio$^2$-yTP was incorporated into RNA opposite s in the template DNA (FIG. 19, Lane 12). Also, in the presence of ATP and GTP together with UTP and/or CTP, Bio$^2$-yTP was competitively and selectively incorporated opposite s in the template (FIG. 19, Lanes 14, 16, 18). Moreover, there was no misincorporation of Bio$^2$-y opposite natural nucleotides in the template (FIG. 19, Lane 20), indicating that Bio$^2$-y could be site-selectively introduced into RNA.

The efficiency of transcription reaction using s:Bio-y or s:Bio2-y base pairing was calculated by comparison of bands of the full-length 17-mer RNAs. As a result, when the efficiency of transcription reaction using natural base pairing was set to 100%, the efficiency was about 50% in the case of using s:Bio-y or s:Bio$^2$-y base pairing (FIG. 19, Lanes 18, 19, 21).

References

The following documents are incorporated herein by reference in their entirety.

1. Battersby, T. R., Ang, D. N., Burgstaller, P., Jurczyk, S. C., Bowser, M. T., Buchanan, D. D., Kennedy, R. T. & Benner, S. A. (1999) Quantitative Analysis of Receptors for Adenosine Nucleotides Obtained via In vitro Selection from a Library Incorporating a Cationic Nucleotide Analog. J. Am. Chem. Soc. 121, 9781-9789.
2. Campbell, S. L., Khosravi-Far, R., Rossman, K. L., Clark, G. J. & Der, C. J. (1998) Increasing complexity of Ras signaling. Oncogene 17, 1395-1413.
3. Chen, P. S., Toribara, T. Y. & Warner, H. (1956) Microdetermination of Phosphorus. Anal. Chem. 28, 1756-1758.
4. Ellington, A. D. & Szostak, J. W. (1990) In vitro selection of RNA molecules that bind specific ligands. Nature 346, 818-822.
5. Fang, X., Cao, Z., Beck, T. & Tan, W. (2001) Molecular aptamer for real-time oncoprotein platelet-derived growth factor monitoring by fluorescence anisotropy. Anal. Chem. 73, 5752-5757.
6. Fujiwara, T., Kimoto, M., Sugiyama, H., Hirao, I. & Yokoyama, S. (2001) Synthesis of 6-(2-Thienyl)purine Nucleoside Derivatives That Form Unnatural Base Pairs with Pyridin-2-one Nucleosides. Bioorg. Med. Chem. Lett. 11, 2221-2223.
7. Golden, M. C., Collins, B. D., Willis, M. C. & Koch, T. H. (2000) Diagnostic potential of PhotoSELEX-evolved ssDNA aptamers. J. Biotechnol. 81, 167-178.
8. Hirao, I., Madin, K., Endo, Y., Yokoyama, S. & Ellington, A.D. (2000) RNA aptamers that Bind to and Inhibit the Ribosome-inactivating Protein, Pepocin. J. Biol. Chem. 275, 4943-4948.
9. Hirao, I., Nojima, T., Mitsui, T. & Yokoyama, S. (2001) Synthesis of DNA templates containing the Fifth base, 2-Amino-6-(dimethylamino)purine, for Specific Transcription Involving Unnatural Base Pairs. Chem. Lett. 914-915.
10. Hirao, I., Ohtsuki, T., Fujiwara, T., Mitsui, T., Yokogawa, T., Okuni, T., Nakayama, K., Takio, K., Yabuki, T., Kigawa, T., Kodama, K., Yokogawa, T., Nishikawa, K. & Yokoyama, S. (2002) An unnatural base pair for incorporating amino acid analogs into proteins. Nat. Biotechnol. 20, 177-182.
11. Inouye, K., Mizutani, S., Koide, H. & Kaziro, Y. (2000) Formation of the Ras Dimer Is Essential for Raf-1 Activation. J. Biol. Chem. 275, 3737-3740.
12. Ishikawa, M., Hirao, I. & Yokoyama, S. (2000) Synthesis of 3-(2-deoxy-β-D-ribofuranosyl)pyridin-2-one and 2-amino-6-(N,N-dimethylamino)-9-(2-deoxy-β-D-ribofuranosyl) purine derivatives for an unnatural base pair. Tetrahedron. Lett. 41, 3931-3034.
13. Jensen, K. B., Atkinson., B. L., Willis, M. C., Koeh, T. D. & Gold, L. (1995) Using in vitro selection to direct the covalent attachment of human immunodeficiency virus type 1 Rev protein to high-affinity RNA ligands. Proc. Natl. Acad. Sci. USA 92, 12220-12224.
14. Jhaveri, S., Rajendran, M. & Ellington, A. D. (2000) In vitro selection of signaling aptamers. Nat. Biotechnol. 18, 1293-1297.
15. Kolch, W. (2000) Meaningful relationships: the regulation of the Ras/Raf/MEK/ERK pathway by protein interactions. Biochem. J. 351, 289-305.
16. Koyama, S., Chen, Y. W., Ikeda, M., Muslin, A. J., Williams, L. T. & Kikuchi, A. (1996) Ras-interacting domain of RGL blocks Ras-dependent signal transduction in *Xenopus oocytes*. FEBS Lett. 380, 113-117.
17. Latham, J. A., Johnson, R. & Toole, J. J. (1994) The application of a modified nucleotide in aptamer selection: novel thrombin aptamers containing 5-(1-pentynyl)-2'-deoxyuridine. Nucleic Acids Res. 22, 2817-2822.
18. Ludwig. J., Eckstein, F., J. Org. Chem., 1989, 54, 631-635.
19. Matulic-Adamic, J., Beigelman, L., (1997) Tetrahedron Lett., 38, 203-206.
20. Meisenheimer, K. M. & Koch, T. H. (1997) Photocross-Linking of Nucleic Acids to Associated Proteins. Crit. Rev. Biochem. Mol. Biol. 32, 101-40.

21. Morales, J. C. & Kool, E. T. (1999) Minor Groove Interactions between Polymerase and DNA: More Essential to Replication than Watson-Crick Hydrogen Bonds? J. Am. Chem. Soc. 121, 2323-2324.
22. Ohtsuki, T., Kimoto, M., Ishikawa, M., Mitsui, T., Hirao, I. & Yokoyama, S. (2001) Unnatural base pairs for specific transcription. Proc. Natl. Acad. Sci. USA 98, 4922-4925.
23. Piccirilli, J. A., Krauch, T., Moroney, S. E. & Benner, S. A. (1990) Enzymatic incorporation of a new base pair into DNA and RNA extends the genetic alphabet. Nature 343, 33-37.
24. Piccirilli, J. A., Moroney, S. E. & Benner, S. A. (1991) A C-nucleotide base pair: methylpseudouridine-directed incorporation of formycin triphosphate into RNA catalyzed by T7 RNA polymerase. Biochemistry 30, 10350-10356.
25. Rapp, U. R., Heidecker, G., Huleihel, M., Cleverland, J. L., Choi, W. C., Pawson, T., Ihle, J. N. & Anderson, W. B. (1988) raf family serine/threonine protein kinases in mitogen signal transduction. Cold Spring Harb. Symp. Quant. Biol. 53, 173-184.
26. Switzer, C. Y., Moreney, S. E. & Benner, S. A. (1993) Enzymatic Recognition of the Base Pair between Isocytidine and Isoguanosine. Biochemistry 32, 10489-10496.
27. Tae, E. L., Wu, Y., Xia, G., Schultz, P. G. & Romesberg, F. E. (2001) Efforts toward Expansion of the Genetic Alphabet: Replication of RNA with Three Base Pairs. J. Am. Chem. Soc. 123, 7439-7440.
28. Wu, Y., Ogawa, A. K., Berger, M., McMinn, D. L., Schultz, P. G. & Romesberg, F. E. (2000) Efforts toward Expansion of the Genetic Alphabet: Optimization of Interbase Hydrophobic Interactions. J. Am. Chem. Soc. 122, 7621-7632.
29. Yamamoto, R., Baba, T. & Kumar, P. K. (2000) Molecular beacon aptamer fluorescences in the presence of Tat protein of HIV-1. Genes Cells. 5, 389-396.

The invention claimed is:

1. A nucleoside or nucleotide having a 5-substituted-2-oxo(1H)-pyridin-3-yl group as a base, wherein the 5-position of the base is substituted with a substituent selected from the group consisting of the following:
 1) a photoreactive group selected from iodine and bromine;
 2) biotin or a derivative thereof;
 3) a fluorescent molecule selected from fluorescein, 6-carboxyfluorescein, and tetramethyl-6-carboxyrhodamine; and
 4) an aminoalkyl linker or an aminoalkenyl linker linked to biotin, dichloroacetyl group, fluorescein, 6-carboxyfluorescein, tetramethyl-6-carboxyrhodamine, or derivatives thereof.

2. The nucleoside or nucleotide according to claim 1, wherein the 5-position of the base is substituted with 1) a photoreactive group selected from iodine and bromine, or 2) biotin or a derivative thereof.

3. The nucleoside or nucleotide according to claim 1 or 2, wherein the 5-position of the base is substituted with iodine or a biotin derivative.

4. A nucleic acid incorporating a nucleoside or nucleotide having a 5-substituted-2-oxo(1H)-pyridin-3-yl group as a base, wherein the 5-position of the base is substituted with a substituent selected from the group consisting of the following:
 1) a photoreactive group selected from iodine and bromine;
 2) biotin or a derivative thereof;
 3) a fluorescent molecule selected from fluorescein, 6-carboxyfluorescein, and tetramethyl-6-carboxyrhodamine, and derivatives thereof; and
 4) an aminoalkyl linker or an aminoalkenyl linker linked to biotin, dichloroacetyl group, fluorescein, 6-carboxyfluorescein, tetramethyl-6-carboxyrhodamine, or derivatives thereof.

5. The nucleic acid according to claim 4, wherein the nucleotide forms a base pair with a nucleotide having a 6-substituted 2-amino-purin-9-yl group as a base.

6. The nucleic acid according to claim 5, wherein the 6-substituted 2-amino-purin-9-yl group is a 2-amino-6-(2-thienyl)purin-9-yl group or a 2-amino-6-(dimethylamino)-purin-9-yl group.

7. The nucleic acid according to claim 4, which is suitable for use as antisense DNA or RNA, a ribozyme or an aptamer.

8. The nucleic acid according to claim 4, which encodes all or part of a protein or peptide.

9. A method for preparing a prepared nucleic acid comprising:
 effecting transcription, replication or reverse transcription by using, as a template, a template nucleic acid containing a template nucleotide having a 6-substituted 2-amino-purin-9-yl group as a base in the presence of the nucleotide according to claim 1 or 2, thereby incorporating said nucleotide as a base into said prepared nucleic acid at a site complementary to said template nucleotide having said 6-substituent 2-amino-purin-9-yl group in said template nucleic acid.

10. The nucleic acid according to claim 4, wherein the 5-position of the base is substituted with 1) a photoreactive group selected from iodine and bromine, or 2) biotin or a derivative thereof.

11. The nucleic acid according to claim 4, wherein the 5-position of the base is substituted with iodine or a biotin derivative.

12. The nucleoside or nucleotide according to claim 1, wherein the 5-position of the base is substituted with a substituent selected from the group consisting of:
 1) a photoreactive group selected from iodine and bromine;
 2) biotin;
 3) a fluorescent molecule selected from fluorescein, 6-carboxyfluorescein, and tetramethyl-6-carboxyrhodamine; and
 4) an aminoalkyl linker or an aminoalkenyl linker linked to biotin, dichloroacetyl group, fluorescein, 6-carboxyfluorescein, or tetramethyl-6-carboxyrhodamine.

13. The nucleic acid according to claim 4, wherein the 5-position of the base is substituted with a substituent selected from the group consisting of:
 1) a photoreactive group selected from iodine and bromine;
 2) biotin;
 3) a fluorescent molecule selected from fluorescein, 6-carboxyfluorescein, and tetramethyl-6-carboxyrhodamine; and
 4) an aminoalkyl linker or an aminoalkenyl linker linked to biotin, dichloroacetyl group, fluorescein, 6-carboxyfluorescein, or tetramethyl-6-carboxyrhodamine.

14. The method according to claim 9, wherein the 5-position of the base is substituted with a substituent selected from the group consisting of:
 1) a photoreactive group selected from iodine and bromine;
 2) biotin;
 3) a fluorescent molecule selected from fluorescein, 6-carboxyfluorescein, and tetramethyl-6-carboxyrhodamine; and
 4) an aminoalkyl linker or an aminoalkenyl linker linked to biotin, dichloroacetyl group, fluorescein, 6-carboxyfluorescein, or tetramethyl-6-carboxyrhodamine.

15. A nucleoside or nucleotide having a 5-substituted-2-oxo(1H)-pyridin-3-yl group as a base, represented by the formula:

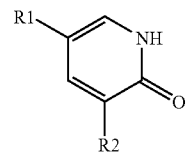

wherein R1 at the 5-position is substituted with a substituent selected from the group consisting of the following:

1) a photoreactive group selected from iodine and bromine;
2) biotin, an ethylenic linker linked to biotin, an acetylenic linker linked to biotin, an aminoalkyl linker linked to biotin, and an aminoalkenyl linker linked to biotin;
3) a fluorescent molecule selected from fluorescein, 6-carboxyfluorescein and tetramethyl-6-carboxyrhodamine; and
4) an aminoalkyl linker or an aminoalkenyl linker linked to fluorescein, 6-carboxyfluorescein, or tetramethyl-6-carboxyrhodamine;

and wherein R2 is selected from the group consisting of the following:
1) a ribose or phosphorylated ribose; and
2) a deoxyribose or a phosphorylated deoxyribose.

16. The nucleoside or nucleotide according to claim 15, wherein the 5-position of the base is substituted with 1) a photoreactive group selected from iodine and bromine or 2) biotin, an ethylenic linker linked to biotin, an acetylenic linker linked to biotin, an aminoalkyl linker linked to biotin, or an aminoalkenyl linker linked to biotin.

17. The nucleoside or nucleotide according to claim 15, wherein the 5-position of the base is substituted with biotin.

18. The nucleoside or nucleotide according to claim 15, wherein the 5-position of the base is substituted with iodine.

19. The nucleoside or nucleotide according to claim 15, wherein the 5-position of the base is substituted with an ethylenic linker linked to biotin or an acetylenic linker linked to biotin.

20. The nucleoside or nucleotide according to claim 15, wherein the nucleoside or nucleotide is selected from the group consisting of:
1) biotinylated 5-(3-amino-1-propenyl)-3-(β-D-ribofuranosyl)-2-pyridone,
2) biotinylated 5-(3-amino-1-propen-2-yl)-3-(β-D-ribofuranosyl)-2-pyridone,
3) biotinylated 5-(3-amino-1-propenyl)-3-(β-D-ribofuranosyl)-2-pyridone 5'-triphosphate,
4) biotinylated 5-(3-amino-1-propen-2-yl)-3-(β-D-ribofuranosyl)-2-pyridone 5'-triphosphate,
5) biotinylated 5-(3-amino-1-propynyl)-3-(β-D-ribofuranosyl)-2-pyridone, and
6) biotinylated 5-(3-amino-1-propynyl)-3-(β-D-ribofuranosyl)-2-pyridone 5'-triphosphate.

21. A nucleoside or nucleotide having a 5-substituted-2-oxo(1H)-pyridin-3-yl group as a base, represented by the formula:

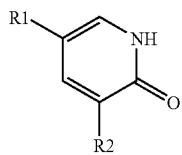

wherein R1 at the 5-position is substituted with an ethylenic linker linked to a dichloroacetyl group or an acetylenic linker linked to a dichloroacetyl group, and wherein R2 is selected from the group consisting of the following:

1) a ribose or phosphorylated ribose; and
2) a deoxyribose or a phosphorylated deoxyribose.

22. A nucleic acid incorporating at least one nucleoside or nucleotide having a 5-substituted-2-oxo(1H)-pyridin-3-yl group as a base, represented by the formula:

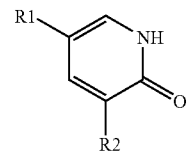

wherein R1 at the 5-position is substituted with a substituent selected from the group consisting of the following:
1) a photoreactive group selected from iodine and bromine;
2) biotin, an aminoalkyl linker linked to biotin, or an aminoalkenyl linker linked to biotin;
3) a fluorescent molecule selected from fluorescein, 6-carboxyfluorescein and tetramethyl-6-carboxyrhodamine; and
4) an aminoalkyl linker or an aminoalkenyl linker linked to fluorescein, 6-carboxyfluorescein, or tetramethyl-6-carboxyrhodamine;

and wherein R2 is selected from the group consisting of the following:
1) a ribose or phosphorylated ribose; and
2) a deoxyribose or phosphorylated deoxyribose.

23. The nucleic acid according to claim 22, wherein the nucleoside or nucleotide at the 5-position of the base, is substituted with 1) a photoreactive group selected from iodine and bromine or 2) biotin, an aminoalkyl linker linked to biotin, or an aminoalkenyl linker linked to biotin.

24. The nucleic acid according to claim 22, wherein the 5-position of the base is substituted with biotin.

25. The nucleic acid according to claim 22, wherein the 5-position of the base is substituted with iodine.

26. The nucleic acid according to claim 22, wherein the nucleotide forms a base pair with a nucleotide having a 6-substituted 2-amino-purin-9-yl group as a base.

27. The nucleic acid according to claim 26, wherein the 6-substituted 2-amino-purin-9-yl group is a 2-amino-6-(2-thienyl)purin-9-yl group or a 2-amino-6-(2-dimethylamino)-purin-9-yl group.

28. The nucleic acid according to claim 22, wherein the nucleic acid is suitable for use as an antisense DNA or RNA, a ribozyme, or an aptamer.

29. The nucleic acid according to claim 22, wherein the nucleic acid encodes all or part of a protein or peptide.

30. A method for preparing a nucleic acid comprising:
effecting transcription, replication or reverse transcription by using a template nucleic acid containing a template nucleotide having a 6-substituted 2-amino-purin-9-yl group as a base in the presence of the nucleotide according to claim 15, thereby incorporating said nucleotide as a base into said prepared nucleic acid at a site which is complementary to said template nucleotide contained in said template nucleic acid.

* * * * *

SEQUENCE LISTING

```
<160> NUMBER OF SEQ ID NOS: 14

<210> SEQ ID NO 1
<211> LENGTH: 100
<212> TYPE: RNA
<213> ORGANISM: Artificial sequence
<220> FEATURE:
<223> OTHER INFORMATION: RNA aptamer

<400> SEQUENCE: 1
gggaguggag gaauucaucg aggcauaugu cgacuccguc uuccuucaaa ccaguuauaa      60
auugguuuua gcauaugccu uagcgacagc aagcuucugc                          100

<210> SEQ ID NO 2
<211> LENGTH: 39
<212> TYPE: DNA
<213> ORGANISM: Artificial sequence
<220> FEATURE:
<223> OTHER INFORMATION: Designed primer for PCR

<400> SEQUENCE: 2
ggtaatacga ctcactatag ggagtggagg aattcatcg                            39

<210> SEQ ID NO 3
<211> LENGTH: 29
<212> TYPE: DNA
<213> ORGANISM: Artificial sequence
<220> FEATURE:
<223> OTHER INFORMATION: Designed primer for PCR

<400> SEQUENCE: 3
gcagaagctt gctgtcgcta aggcatatg                                       29

<210> SEQ ID NO 4
<211> LENGTH: 29
<212> TYPE: DNA
<213> ORGANISM: Artificial sequence
<220> FEATURE:
<223> OTHER INFORMATION: Designed primer for PCR
<220> FEATURE:
<221> NAME/KEY: misc_feature
<222> LOCATION: (17)..(17)
<223> OTHER INFORMATION: n is an unnatural base equivalent to a 2-amino-
      6-(2-thienyl)-purine-9-yl group
```

<400> SEQUENCE: 4
gcagaagctt gctgtcncta aggcatatg                                29

<210> SEQ ID NO 5
<211> LENGTH: 29
<212> TYPE: DNA
<213> ORGANISM: Artificial sequence
<220> FEATURE:
<223> OTHER INFORMATION: Designed primer for PCR
<220> FEATURE:
<221> NAME/KEY: misc_feature
<222> LOCATION: (14)..(14)
<223> OTHER INFORMATION: n is an unnatural base equivalent to a 2-amino-
      6-(2-thienyl)-purine-9-yl group

<400> SEQUENCE: 5
gcagaagctt gctntcgcta aggcatatg                                29

<210> SEQ ID NO 6
<211> LENGTH: 29
<212> TYPE: DNA
<213> ORGANISM: Artificial sequence
<220> FEATURE:
<223> OTHER INFORMATION: Designed primer for PCR
<220> FEATURE:
<221> NAME/KEY: misc_feature
<222> LOCATION: (9)..(9)
<223> OTHER INFORMATION: n is an unnatural base equivalent to a 2-amino-
      6-(2-thienyl)-purine-9-yl group

<400> SEQUENCE: 6
gcagaagcnt gctgtcgcta aggcatatg                                29

<210> SEQ ID NO 7
<211> LENGTH: 29
<212> TYPE: DNA
<213> ORGANISM: Artificial sequence
<220> FEATURE:
<223> OTHER INFORMATION: Designed primer for PCR
<220> FEATURE:
<221> NAME/KEY: misc_feature
<222> LOCATION: (9)..(9)
<223> OTHER INFORMATION: n is a, g, c, t, unknown or other
<220> FEATURE:
<221> NAME/KEY: misc_feature
<222> LOCATION: (17)..(17)
<223> OTHER INFORMATION: n is an unnatural base equivalent to a 2-amino-
      6-(2-thienyl)-purine-9-yl group

<400> SEQUENCE: 7
gcagaagcnt gctgtcncta aggcatatg                                29

<210> SEQ ID NO 8
<211> LENGTH: 35
<212> TYPE: DNA
<213> ORGANISM: Artificial sequence
<220> FEATURE:
<223> OTHER INFORMATION: Synthesized template strand for transcription
<220> FEATURE:
<221> NAME/KEY: misc_feature
<222> LOCATION: (29)..(29)
<223> OTHER INFORMATION: n is an unnatural base equivalent to a 2-amino-
      6-(2-thienyl)-purine-9-yl group

<400> SEQUENCE: 8
tattatgctg agtgatatcc ctccttctnt ctcgt                         35

<210> SEQ ID NO 9
<211> LENGTH: 35

```
<212> TYPE: DNA
<213> ORGANISM: Artificial sequence
<220> FEATURE:
<223> OTHER INFORMATION: Synthesized template strand for transcription

<400> SEQUENCE: 9
tattatgctg agtgatatcc ctccttctat ctcgt                                    35

<210> SEQ ID NO 10
<211> LENGTH: 28
<212> TYPE: DNA
<213> ORGANISM: Artificial sequence
<220> FEATURE:
<223> OTHER INFORMATION: Designed primer for transcription

<400> SEQUENCE: 10
ataatcgact ctactatagg gaggaaga                                            28

<210> SEQ ID NO 11
<211> LENGTH: 200
<212> TYPE: RNA
<213> ORGANISM: Artificial sequence
<220> FEATURE:
<223> OTHER INFORMATION: RNA aptamer 9A

<400> SEQUENCE: 11
gggaguggag gaauucaucg aggcauaugu cgacuccguc uuccuucaaa ccaguuauaa          60
auugguuuua gcauaugccu uagcgacagc aagcuucugc gggaguggag gaauucaucg        120
aggcauaugu cgacuccguc uuccuucaaa ccaguuauaa auugguuuua gcauaugccu        180
uagcgacagc aagcuucugc                                                   200

<210> SEQ ID NO 12
<211> LENGTH: 101
<212> TYPE: RNA
<213> ORGANISM: Artificial sequence
<220> FEATURE:
<223> OTHER INFORMATION: RNA aptamer 2x9A

<400> SEQUENCE: 12
gggaguggag gaauucaucg aggcaucugg gaacccuauc uugcuuuugg uagcuguauu         60
caccuguaac agcauaugcc uuagcgacag caagcuucug c                           101

<210> SEQ ID NO 13
<211> LENGTH: 15
<212> TYPE: RNA
<213> ORGANISM: Artificial sequence
<220> FEATURE:
<223> OTHER INFORMATION: Synthetic RNA 15-mer
<220> FEATURE:
<221> NAME/KEY: misc_feature
<222> LOCATION: (11)..(11)
<223> OTHER INFORMATION: n is a, g, c, u, unknown or other

<400> SEQUENCE: 13
gggaggaaga nagag                                                         15

<210> SEQ ID NO 14
<211> LENGTH: 17
<212> TYPE: RNA
<213> ORGANISM: Artificial sequence
<220> FEATURE:
<223> OTHER INFORMATION: Synthetic RNA 17-mer
<220> FEATURE:
<221> NAME/KEY: misc_feature
<222> LOCATION: (11)..(11)
```

```
<223> OTHER INFORMATION: n is a, g, c, u, unknown or other

<400> SEQUENCE: 14
gggaggaaga nagagca                                                     17
```